US010960200B2

(12) United States Patent
Nestler et al.

(10) Patent No.: US 10,960,200 B2
(45) Date of Patent: Mar. 30, 2021

(54) HEART PUMP WITH IMPELLER AXIAL POSITION CONTROL

(71) Applicant: BiVACOR Inc., Houston, TX (US)

(72) Inventors: Frank Nestler, Annaberg-Buchholz (DE); Nicholas Greatrex, Cornubia (AU); Daniel Timms, Long Beach, CA (US); Matthias Kleinheyer, Aspley (AU)

(73) Assignee: BiVACOR Inc., Houston, TX (US)

( * ) Notice: Subject to any disclaimer, the term of this patent is extended or adjusted under 35 U.S.C. 154(b) by 0 days.

(21) Appl. No.: 16/028,957

(22) Filed: Jul. 6, 2018

(65) Prior Publication Data

US 2018/0369466 A1 Dec. 27, 2018

Related U.S. Application Data

(63) Continuation of application No. PCT/US2017/012508, filed on Jan. 6, 2017.
(Continued)

(51) Int. Cl.
*A61M 1/10* (2006.01)
*A61M 60/82* (2021.01)
(Continued)

(52) U.S. Cl.
CPC ............... *A61M 60/82* (2021.01); *A61F 2/24* (2013.01); *A61M 60/122* (2021.01);
(Continued)

(58) Field of Classification Search
CPC ........... A61M 1/10; F04D 13/06; F04D 29/04
(Continued)

(56) References Cited

U.S. PATENT DOCUMENTS 2,700,343 A 1/1955 Pezzillo, Jr.
4,135,253 A 1/1979 Reich et al.
(Continued)

FOREIGN PATENT DOCUMENTS

CA 2638958 C 11/2011
CN 101873870 A 10/2010
(Continued)

OTHER PUBLICATIONS

Amano, et al., An ultrasonic actuator with multi-degree of freedom using bending and longitudinal vibrations of a single stator; IEEE Ultrason. Symp. Proc.; pp. 667-670; 1998.
(Continued)

*Primary Examiner* — Jon Eric C Morales
(74) *Attorney, Agent, or Firm* — Goodwin Procter LLP

(57) ABSTRACT

A heart pump including a housing defining a cavity including at least one inlet and at least one outlet, an impeller provided within the cavity, the impeller including vanes for urging fluid from the inlet to the outlet upon rotation of the impeller, a drive that rotates the impeller within the cavity, a magnetic bearing including at least one bearing coil that controls an axial position of the impeller within the cavity, a sensor that senses an axial position of the impeller within the cavity and a controller. The controller includes an electronic processing device that, in response to a change in axial hydraulic forces on the impeller determines an axial position of the impeller within the cavity, determines a reference power in accordance with the determined axial position and controls the magnetic bearing to cause the impeller to move until a bearing power indicator indicative of the power used by the magnetic bearing reaches the reference power.

20 Claims, 21 Drawing Sheets

Related U.S. Application Data

(60) Provisional application No. 62/275,754, filed on Jan. 6, 2016, provisional application No. 62/275,723, filed on Jan. 6, 2016, provisional application No. 62/275,744, filed on Jan. 6, 2016.

(51) Int. Cl.

| | |
|---|---|
| *A61M 60/50* | (2021.01) |
| *A61M 60/122* | (2021.01) |
| *A61M 60/148* | (2021.01) |
| *A61M 60/205* | (2021.01) |
| *A61M 60/419* | (2021.01) |
| *A61M 60/422* | (2021.01) |
| *A61M 60/857* | (2021.01) |
| *A61F 2/24* | (2006.01) |
| *F04D 1/00* | (2006.01) |
| *F04D 29/048* | (2006.01) |
| *F04D 29/24* | (2006.01) |
| *F04D 29/42* | (2006.01) |
| *A61M 60/824* | (2021.01) |

(52) U.S. Cl.
CPC ........ *A61M 60/148* (2021.01); *A61M 60/205* (2021.01); *A61M 60/419* (2021.01); *A61M 60/422* (2021.01); *A61M 60/50* (2021.01); *A61M 60/857* (2021.01); *F04D 1/00* (2013.01); *F04D 29/048* (2013.01); *F04D 29/242* (2013.01); *F04D 29/4293* (2013.01); *A61M 60/824* (2021.01); *A61M 2205/3334* (2013.01); *A61M 2205/3365* (2013.01); *A61M 2206/14* (2013.01); *A61M 2206/20* (2013.01); *A61M 2230/04* (2013.01); *A61M 2230/30* (2013.01)

(58) Field of Classification Search
USPC .................. 417/356, 420; 415/900; 623/3.11
See application file for complete search history.

(56) References Cited

U.S. PATENT DOCUMENTS

| | | |
|---|---|---|
| 4,589,822 A | 5/1986 | Clausen et al. |
| 5,041,934 A | 8/1991 | Stefansky |
| 5,195,877 A | 3/1993 | Kletschka |
| 5,601,418 A | 2/1997 | Ohara et al. |
| 5,613,935 A | 3/1997 | Jarvik |
| 5,725,357 A | 3/1998 | Nakazeki et al. |
| 5,840,070 A | 11/1998 | Wampler |
| 5,851,174 A | 12/1998 | Jarvik et al. |
| 5,890,883 A | 4/1999 | Golding et al. |
| 5,928,131 A | 7/1999 | Prem |
| 5,971,023 A | 10/1999 | Clague et al. |
| 6,017,903 A | 1/2000 | Slusher et al. |
| 6,048,363 A | 4/2000 | Nagyszalanczy et al. |
| 6,179,773 B1 | 1/2001 | Prem et al. |
| 6,220,832 B1 | 4/2001 | Schob |
| 6,227,797 B1 | 5/2001 | Watterson et al. |
| 6,234,772 B1 | 5/2001 | Wampler et al. |
| 6,264,635 B1 | 7/2001 | Wampler et al. |
| 6,293,901 B1 | 9/2001 | Prem |
| 6,312,443 B1 | 11/2001 | Stone |
| 6,351,048 B1 | 2/2002 | Schob et al. |
| 6,394,769 B1 | 5/2002 | Bearnson et al. |
| 6,422,838 B1 | 7/2002 | Sloteman |
| 6,527,698 B1 | 3/2003 | Kung et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,626,644 B2 | 9/2003 | Ozaki |
| 6,638,011 B2 | 10/2003 | Woodard et al. |
| 6,664,714 B2 | 12/2003 | Magnussen et al. |
| 6,688,861 B2 | 2/2004 | Wampler |
| 6,690,101 B2 | 2/2004 | Magnussen et al. |
| 6,717,311 B2 | 4/2004 | Locke |
| 6,790,171 B1 | 9/2004 | Grundeman et al. |
| 6,866,625 B1 | 3/2005 | Ayre et al. |
| 6,870,304 B2 | 3/2005 | Magnussen et al. |
| 7,229,474 B2 | 6/2007 | Hoffmann et al. |
| 7,274,131 B2 | 9/2007 | Li et al. |
| 7,435,059 B2 | 10/2008 | Smith et al. |
| 7,439,652 B2 | 10/2008 | Ganor et al. |
| 7,462,019 B1 | 12/2008 | Allarie et al. |
| 7,476,077 B2 | 1/2009 | Woodard et al. |
| 7,645,225 B2 | 1/2010 | Medvedev et al. |
| 7,704,054 B2 | 4/2010 | Horvath et al. |
| 7,914,436 B1 | 3/2011 | Kung |
| 7,931,581 B2 | 4/2011 | Cohn |
| 8,110,967 B2 | 2/2012 | Ting et al. |
| 8,210,829 B2 | 7/2012 | Horvath et al. |
| 8,226,373 B2 | 7/2012 | Yaegashi |
| 8,506,471 B2 | 8/2013 | Bourque |
| 8,551,163 B2 | 10/2013 | Aber et al. |
| 8,613,696 B2 | 12/2013 | Medvedev et al. |
| 8,636,638 B2 | 1/2014 | Timms |
| 8,747,293 B2 | 6/2014 | Arndt et al. |
| 8,834,345 B2 | 9/2014 | Yanai et al. |
| 8,961,388 B2 | 2/2015 | Bourque |
| 9,011,312 B2 | 4/2015 | Bourque |
| 9,095,428 B2 | 8/2015 | Kabir et al. |
| 9,371,826 B2 | 6/2016 | Yanai et al. |
| 9,427,508 B2 | 8/2016 | Reyes et al. |
| 9,433,717 B2 | 9/2016 | Bourque |
| 9,492,601 B2 | 11/2016 | Casas et al. |
| 9,511,179 B2 | 12/2016 | Casas et al. |
| 9,512,852 B2 | 12/2016 | Wampler et al. |
| 9,709,061 B2 | 7/2017 | Yanai et al. |
| 9,801,988 B2 | 10/2017 | Bourque |
| 9,901,666 B2 | 2/2018 | Cotter |
| 10,077,777 B2 | 9/2018 | Horvath et al. |
| 10,086,122 B2 | 10/2018 | Bourque |
| 2002/0094281 A1* | 7/2002 | Khanwilkar .......... F04D 29/048 417/356 |
| 2002/0109621 A1 | 8/2002 | Khair et al. |
| 2003/0023131 A1 | 1/2003 | Antaki |
| 2004/0267344 A1 | 12/2004 | Stett et al. |
| 2005/0214131 A1 | 9/2005 | Miles et al. |
| 2007/0249888 A1 | 10/2007 | Wu et al. |
| 2007/0253842 A1 | 11/2007 | Horvath et al. |
| 2010/0168848 A1 | 7/2010 | Horvath et al. |
| 2011/0118537 A1 | 5/2011 | Wampler |
| 2011/0118619 A1 | 5/2011 | Burton et al. |
| 2011/0148253 A1 | 6/2011 | Friend et al. |
| 2012/0245680 A1* | 9/2012 | Masuzawa .......... A61M 1/1086 623/3.11 |
| 2012/0253103 A1 | 10/2012 | Robert |
| 2012/0289897 A1 | 11/2012 | Friend et al. |
| 2014/0100413 A1 | 4/2014 | Casas et al. |
| 2017/0340788 A1 | 11/2017 | Korakianitis et al. |
| 2018/0185567 A1 | 7/2018 | Madhani et al. |
| 2018/0228955 A1* | 8/2018 | Granegger ............ A61M 1/122 |
| 2018/0311422 A1* | 11/2018 | Greatrex ............ A61M 1/1015 |

FOREIGN PATENT DOCUMENTS

| | | |
|---|---|---|
| CN | 102458498 B | 6/2015 |
| CN | 102711862 B | 12/2015 |
| EP | 1065383 A1 | 1/2001 |
| EP | 1188453 A1 | 3/2002 |
| EP | 1273096 B1 | 11/2005 |
| EP | 1630897 A1 | 3/2006 |
| EP | 1674119 A1 | 6/2006 |
| EP | 1495773 A3 | 11/2006 |
| EP | 1721346 B1 | 10/2007 |
| EP | 2538086 A4 | 4/2015 |
| JP | 7255834 | 10/1995 |
| JP | 2001061957 A | 3/2001 |
| JP | 2001-224568 A | 8/2001 |
| JP | 2003-230547 A | 8/2003 |
| JP | 2004-61251 A | 2/2004 |
| JP | 2005-282675 A | 10/2005 |
| JP | 3930834 B2 | 6/2007 |

(56) References Cited

FOREIGN PATENT DOCUMENTS

| | | |
|---|---|---|
| JP | 2009-011767 A | 1/2009 |
| WO | WO-00/32256 A1 | 6/2000 |
| WO | WO-00/32257 A1 | 6/2000 |
| WO | WO-2002-053028 A8 | 12/2002 |
| WO | WO-2004-032738 A1 | 4/2004 |
| WO | WO-2004-043252 A1 | 5/2004 |
| WO | WO-2004-047636 A1 | 6/2004 |
| WO | WO-2004098677 A1 | 11/2004 |
| WO | WO-2004-098389 A3 | 3/2005 |
| WO | WO-2006053384 A1 | 5/2006 |
| WO | WO-2007/056493 A1 | 5/2007 |
| WO | WO-2007/084339 A3 | 1/2008 |
| WO | WO-2009/058726 A1 | 5/2009 |
| WO | WO-2010/118475 A1 | 10/2010 |
| WO | WO-2010/118476 A1 | 10/2010 |
| WO | WO-2011/026187 A1 | 3/2011 |
| WO | WO-2011/054545 A1 | 5/2011 |
| WO | WO-2013/033783 A1 | 3/2013 |
| WO | WO-2017/120453 A1 | 7/2017 |
| WO | WO-2017/120451 A3 | 8/2017 |
| WO | WO-2017/120449 A3 | 11/2017 |

OTHER PUBLICATIONS

Gaddum, Nicholas Richard, "Passive Control of a Bi-Ventricular Assist Device: An experimental and Numerical Investigation", (Thesis), Queensland University of Technology 2008, Ch. 3, sections 3.4.3.1, 3.4.3.4, 3.6 to 3.7 & Figs. 3-12 to 3-14, 3-16, 3-18, 3-23, 3-25 to 3-27, 3-35 to 3-36; Ch. 8, section 8.2.1.
Gouda et al.; A miniaturization of the multi-degree-of-freedom ultrasonic actuator using a small cylinder fixed on a substrate; Ultrasonics; 44 supp. 1; pp. e617-e620; Dec. 22, 2006.
Greatrex N. et al. 'Axial magnetic bearing . . . ', 2010, IEEE Transactions in Biomedical Eng', vol. 57(3), pp. 714-721.
Kanda et al. A micro ultrasonic motor using a micro-machined cylindrical bulk PZT transducer; Sensors and Actuators; 127; pp. 131-138; Dec. 19, 2009.
Kawano et al.; Application of a multi-DOF ultrasonic servomotor in an auditory tele-existence robot; IEEE Trans. Robotics; 21 (5); pp. 790-800; Oct. 2005.
Khoo et al.; Triple degree-of-freedom piezoelectric micromotor via flexural-axial coupled vibration; IEEE Transactions on ultrasonics, Ferroelectrics, and Frequency Control; 56(8); pp. 1716-1724; Aug. 2009.
Maslen E. et cl. 'Feedback Control Applications in Artificial Hearts . . . ' 1998 IEEE Control Systems Mag, vol. 18(6), pp. 26-34.
Masuzawa T. et al, 'Magnetically Suspended Centrifugal . . . ' 2002, ASAIO Journal, pp. 437-442.
Masuzawa, T., H. Onuma, and Y. Okada, "Zero Power Control for Magnetically Suspended Artificial Heart." Jido Seigyo Rengo Koenkai Koen Ronbunshu, 2004. 47: p. 322.
Masuzawa, Toru et al., "An Ultradurable and Compact Rotary Blood Pump with a Magnetically Suspended Impeller in the Radial Direction", Artificial Organs, vol. 25, Issue 5, 2001, pp. 395-399, Abstract; Suspension system (pp. 396-397); Discussion (p. 398); Figs. 1-6.

Masuzawa, Toru et al., "Magnetically Suspended Centrifugal Blood Pump with an Axially Levitated Motor", Artificial Organs, vol. 27, Issue 7, 2003, pp. 631-638 Abstract; axially levitated motor (pp. 632-633); Motor design and experimental set-up (pp. 633-634); levitation performance (pp. 634-635); Discussion (pp. 636-638); Figs. 1, 3-5, 8 and 13.
Masuzawa, Toru et al., "Magnetically Suspended Rotary Blood Pump with Radial Type Combined Motor-Bearing", Artificial Organs, vol. 24, Issue 6, 2000, pp. 468-474, Abstract; Suspension control (pp. 468-469); Prototype of the magnetically suspended centrifugal pump (pp. 469-470); Discussion (p. 471); Figs. 1-6.
Morita, et al.; A cylindrical micro ultrasonic motor using PZT thin film deposited by single process hydrothermal method (Ø2.4 mm, L=10 mm stator transducer); IEEE Trans. Ferroelectr. Freq. Contrl; 45(5); pp. 1178-1187; Sep. 1998.
Niwano, et al.; An active dummy head driven by a multi-degree-of-freedom ultrasonic actuator; WCU Conf. Proc. 1597; 2003.
Park, et al.; Study on multi-DOF ultrasonic actuator for laparoscopic instrument; JSME int. J.; 47(2); pp. 574-581; 2004.
Rogers; A diameter 300 pm bragg reflector for acoustic isolation of resonant micro-actuators; J. Micromech. Microeng. 21 (4 ); pp. 1-4; Apr. 2011.
Rogers; Piezoelectric ultrasonic micro-motor system for minimally invasive surgery—the intellimotor; AIP Conf. Proc. 1433 pp. 705-708; 2012.
Rogers; Three degree-of-freedom piezoelectric ultrasonic micro-motor with a major diameter of 350 μm; J. Micromech. Microeng.;20(12); pp. 1-5; Dec. 2010.
Satoshi Ueno et al., "Characteristics of axial force and rotating torque and their control of permanent magnet type axial gap self-bearing motor", Electrical Engineering in Japan, vol. 132, Issue 1, 2000, pp. 81-91 (whole document).
Sin, D.C. et al., "Blood flow in a double output centrifugal artificial heart pump as a biventricular assist device", Anziam J. 48 (CTAC2006), Feb. 27, 2008, pp. C949-C962, Materials and Method section (pp. C952-C955); Figures 2-4.
Takemura et al.; Characterstics of an ultrasonic motor capable of generating a multi-degrees of freedom motion; Proc. IEEE int. Conf. on Robotics and Automation; vol. 4; pp. 3660-3665; Apr. 2000.
Takemura et al.; Control of multi-dof ultrasonic actuator for dexterous surgical instrument; Journal of Sound and Vibration; 311; pp. 652-666; Nov. 26, 2007.
Timms, D.L., "Design, Development and Evaluation of Centrifugal Type Ventricular Assist Devices", (Thesis), Queensland University of Technology, 2005 Ch. 4, sections 4.4.4-3 BiLVAD and 4.4.4 Bi-VAD & Figure 4-20 to 4-21; Ch. 5—VAD Experimental Evaluation; Ch. 6, VAD Summary & Figures 6-1 to 6-8.
Wajchman et al.; An ultrasonic piezoelectric motor utilizing axial-torsional coupling in a pretwisted non-circular cross-sectioned primatic beam; IEEE Transactions of Ultrasonics, Ferroelectrics, and Frequency Control; 55(4); pp. 832-840; Apr. 2008.
Watson Peizoelectric ultrasonic micro/milli-scale actuators; Sensors Actuators; 152; pp. 219-233; Apr. 2, 2009.
Sonune, et al "Performance Investigation of Centrifugal Pump by Varying Blade Angles of the Impeller-A" IJCET INPRESSO Special Issue—7 (Mar. 2017), pp. 399-401.
Gulich, Gentrifugal pumps 2nd Ed (2010), pp. 352-357.

* cited by examiner

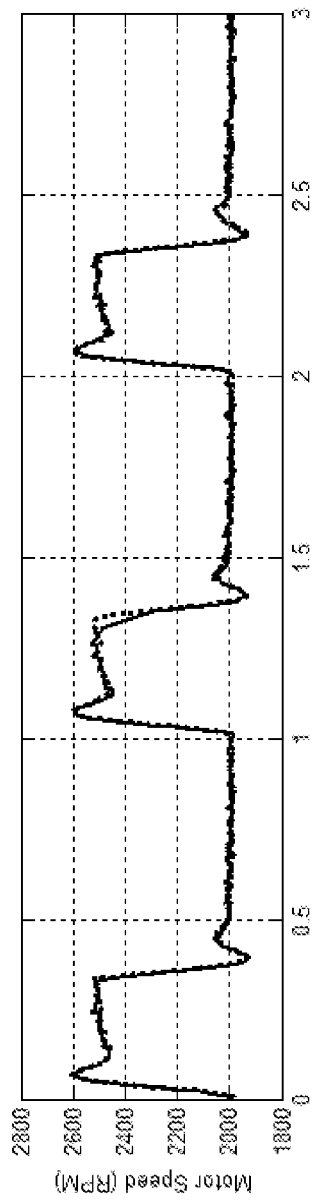
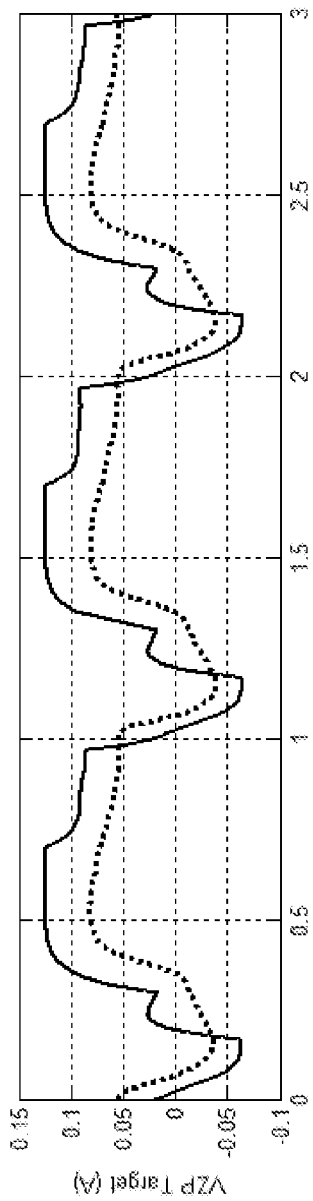
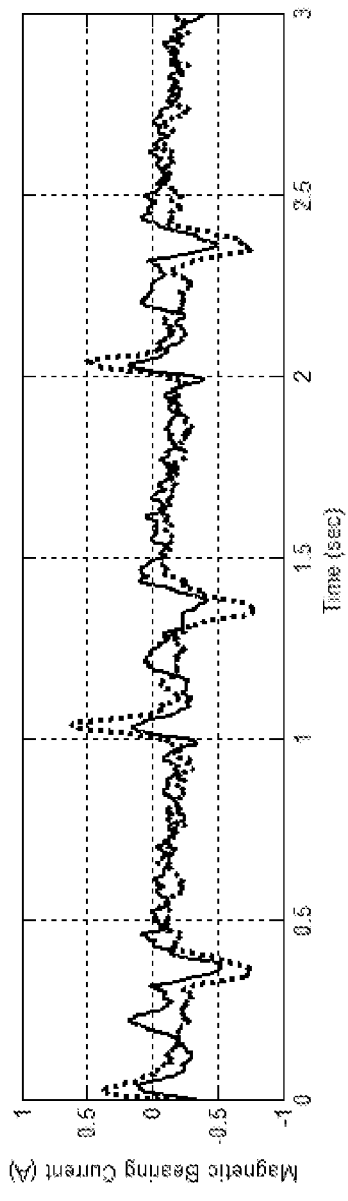
Fig. 11A
Fig. 11B
Fig. 11C

HEART PUMP WITH IMPELLER AXIAL POSITION CONTROL

CROSS-REFERENCE TO RELATED APPLICATIONS

This application claims the benefit of priority under 35 U.S.C. § 120 to International Patent Application No. PCT/US2017/012508 entitled "Heart Pump With Impeller Axial Position Control," filed on Jan. 6, 2017 which claims priority under 35 U.S.C. § 119 to U.S. Provisional Patent Application No. 62/275,754 entitled "Heart Pump," filed on Jan. 6, 2016; U.S. Provisional Patent Application No. 62/275,723 entitled "Heart Pump Impeller Rotational Speed Control," filed on Jan. 6, 2016; and U.S. Provisional Patent Application No. 62/275,744 entitled "Heart Pump With Impeller Axial Position Control," filed on Jan. 6, 2016, the contents of all of which are incorporated herein by reference in their entireties.

BACKGROUND OF THE INVENTION

The present invention relates to a heart pump and in particular to a method of controlling an axial position of an impeller in a heart pump.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The use of rotary impeller based mechanical pumps to treat heart failure is increasing as the general population ages and the number of donor organs for heart transplantation remains limited. Devices can be used to bridge a patient to heart transplant, to recovery, or indeed as a destination alternative.

WO2004098677 and WO2006053384A1 each describe a double sided impeller that rotates at a common speed, with each side of the impeller respectively configured for left and right heart assistance. This effectively introduces an inherent problem regarding the ability to independently control and thus balance the outflow from the left and right sides of the device, i.e. an increase in impeller rotational speed with produce a corresponding increase in outflow from both cavities.

WO2006053384A1 addressed this issue by introducing the ability to axially displace the rotating impeller within the cavity so as to simultaneously alter the relative efficiencies of each side of the device. However, when the control method used to achieve this axial displacement is active, such pumps require the use of feedback signals from pressure sensors and the like to actively control and maintain a desired set axial location. This method of control would inherently consume excessive amounts of electrical power and introduce issues relating to the long term reliability of blood contacting sensors.

U.S. Pat. No. 8,636,638 describes a controller for a heart pump that determines movement of an impeller within a cavity in a first axial direction, the cavity including at least one inlet and at least one outlet, and the impeller including vanes for urging fluid from the inlet to the outlet, causing a magnetic bearing to move the impeller in a second axial direction opposite the first axial direction, the magnetic bearing including at least one coil for controlling an axial position of the impeller within the cavity, determining an indicator indicative of the power used by the magnetic bearing and causing the magnetic bearing to control the axial position of the impeller in accordance with the indicator to thereby control a fluid flow between the inlet and the outlet.

U.S. Pat. No. 7,435,059 describes a system for pumping blood to assist or assume the cardiac function of a patient is characterized by a blood pump that exhibits a steep pump curve such that only small changes in pump flow occur for large changes in differential pressure across the pump. The pump therefore exhibits flow-limiting characteristics to protect the physiological system against harmful flow rates. Pump flow may also be limited by controlling the current provided to a driver from a power supply or by suitable restrictions within or external to the pump housing.

This arrangement provides a so called zero power configuration that attempts to minimise the power required by the magnetic bearing used to suspend the rotor. However, this does not provide adequate control of impeller position in all scenarios.

SUMMARY OF THE PRESENT INVENTION

In one broad form, one aspect of the present invention seeks to provide a heart pump including: a housing defining a cavity including at least one inlet and at least one outlet; an impeller provided within the cavity, the impeller including vanes for urging fluid from the inlet to the outlet upon rotation of the impeller; a drive that rotates the impeller within the cavity; a magnetic bearing including at least one bearing coil that controls an axial position of the impeller within the cavity; a sensor that senses an axial position of the impeller within the cavity; and, a controller including an electronic processing device that, in response to a change in axial hydraulic forces on the impeller: determines an axial position of the impeller within the cavity; determines a reference power in accordance with the determined axial position; and, controls the magnetic bearing to cause the impeller to move until a bearing power indicator indicative of the power used by the magnetic bearing reaches the reference power.

In one embodiment the change in hydraulic forces generate a resulting force acting on the impeller in a first axial direction and wherein the controller controls the magnetic bearing to move the impeller in a second axial direction opposite to the first axial direction.

In one embodiment the controller determines changes in axial hydraulic forces within the cavity by at least one of: detecting axial movement of the impeller within the cavity; and, detecting changes in the bearing power indicator required to maintain the impeller at a constant axial position within the cavity.

In one embodiment the controller determines changes in axial hydraulic forces by filtering a bearing current signal using at least one of a low pass filter; a band pass filter; and, a notch filter.

In one embodiment the low pass filter has a cut-off of at least one of: between 0.1-10 Hz, between 1-15 Hz; between 15-30 Hz; approximately 15 Hz; approximately 30 Hz; approximately 1 Hz; and, between 30-100 Hz.

In one embodiment the controller iteratively moves the impeller by repeatedly: controlling the magnetic bearing to move the impeller to a new axial position in accordance with the reference power; and, modifying the reference power in accordance with the new axial position of the impeller.

In one embodiment the controller iteratively moves the impeller until at least one of: the reference power reaches a defined threshold; the axial position of the impeller reaches a defined threshold; and, the hydraulic forces are at least one of: balanced; and, reversed.

In one embodiment the controller modifies the reference power by progressively increasing a magnitude of the reference power by a progressively smaller amount for each iteration.

In one embodiment the controller: controls the magnetic bearing to cause the impeller to move to a target axial position; determines if the bearing power indicator is at the reference power; and, if the bearing power indicator is not at the reference power; determines a new axial position of the impeller; determines a reference power in accordance with the new axial position; uses the reference power to determine a target axial position; and, repeats steps a) to c) until the bearing power indicator reaches the reference power.

In one embodiment the controller includes: a bearing controller that: uses signals from the position sensor to determine the current axial position of the impeller; controls the current supplied to the magnetic bearing to thereby maintain the impeller at a target axial position; and, outputs the bearing power indicator and current axial position; and, a position controller that: uses the bearing power indicator and current axial position of the impeller to determine the target axial position; and, provide the target axial position to the bearing controller.

In one embodiment the power controller includes: a first controller that calculates a reference power using the current axial position of impeller; and, a second controller that determines the target axial position using the reference power and the bearing power indicator.

In one embodiment the controller records an indication of at least one of: the bearing power indicator; and, the axial position of the impeller.

In one embodiment the impeller includes first and second sets of vanes provided on a rotor body, the rotor being positioned within the cavity to define: a first cavity portion having a first inlet and a first outlet, the first set of vanes being provided within the first cavity portion so as to define a first pump that provides at least partial left ventricular function; and, a second cavity portion having a second inlet and a second outlet, the second set of vanes being provided within the second cavity portion so as to define a second pump that provides at least partial right ventricular function.

In one embodiment the axial position of the impeller determines a separation between each set of vanes and a respective cavity surface, the separation being used to control the fluid flows from the inlets to the outlets.

In one embodiment the first and second pumps have respective pump performance curve having different gradients so that a change in rotational speed of the pump causes a change in the relative flows of the first and second pumps.

In one embodiment the drive includes: a number of circumferentially spaced permanent magnets mounted in the rotor of the impeller, adjacent magnets having opposing polarities, at least one drive coil that in use generates a magnetic field that cooperates with the magnetic material allowing the impeller to be rotated.

In one embodiment the magnetic bearing includes: first and second annular magnetic bearing members mounted within and proximate a second face of the rotor, the first magnetic bearing member being provided radially outwardly of the second magnetic bearing member; a number of circumferentially spaced substantially U-shaped bearing stators mounted in the housing proximate a second end of the cavity, each U-shaped bearing stator having first and second bearing stator legs substantially radially aligned with the first and second magnetic bearing members respectively; and, at least one bearing coil on each bearing stator that generates a magnetic field that cooperates with the magnetic bearing members to thereby at least one of: control an axial position of the impeller; and, at least partially restrain radial movement of the impeller.

In one embodiment the drive is positioned at a first end of the cavity and the magnetic bearing is positioned at a second end of the cavity.

In one embodiment the heart pump is at least one of: a ventricular assist device; and, a total artificial heart.

In one broad form, one aspect of the present invention seeks to provide a controller for a heart pump, the controller including an electronic processing device that: determines an axial position of an impeller within a cavity; determines a reference power in accordance with the determined axial position; and, controls a magnetic bearing to cause the impeller to move until a bearing power indicator indicative of the power used by the magnetic bearing reaches the reference power.

In one broad form, one aspect of the present invention seeks to provide a method of controlling a heart pump, the method including: determining an axial position of an impeller within a cavity; determining a reference power in accordance with the determined axial position; and, controlling a magnetic bearing to cause the impeller to move until a bearing power indicator indicative of the power used by the magnetic bearing reaches the reference power.

In one broad form, one aspect of the present invention seeks to provide a heart pump including: a housing defining a cavity including at least one inlet and at least one outlet; an impeller provided within the cavity, the impeller including vanes for urging fluid from the inlet to the outlet upon rotation of the impeller; a drive that rotates the impeller within the cavity; a magnetic bearing including at least one bearing coil that controls an axial position of the impeller within the cavity; and, a controller including an electronic processing device that: determines pump operating parameter changes that will cause a change in at least one of hydraulic forces and motor attractive forces on the impeller; determines a reference power in accordance with the pump operating parameter changes; and, controls the magnetic bearing to cause the impeller to move until a bearing power indicator indicative of the power used by the magnetic bearing reaches the reference power.

In one embodiment the controller: determines a change in rotational speed of the impeller; and, determines the reference power in accordance with the change in rotational speed of the impeller.

In one embodiment the controller controls the magnetic bearing in accordance with the reference power, at least one of: prior to the change in rotational speed of the impeller; and, during the change in rotational speed of the impeller.

In one embodiment the controller: determines an axial position of the impeller within the cavity; and, determines the reference power in accordance with the determined axial position and the pump operating parameter changes.

In one broad form, one aspect of the present invention seeks to provide a controller for a heart pump, the controller including an electronic processing device that: determines pump operating parameter changes that will cause a change in at least one of hydraulic forces and motor attractive forces on an impeller; determines a reference power in accordance with the pump operating parameter changes; and, controls a magnetic bearing to cause the impeller to move until a bearing power indicator indicative of the power used by the magnetic bearing reaches the reference power.

In one broad form, one aspect of the present invention seeks to provide a method for controlling a heart pump, the method including, in an electronic processing device: determining pump operating parameter changes that will cause a change in at least one of hydraulic forces and motor attractive forces on an impeller; determining a reference power in accordance with the pump operating parameter changes; and, controlling a magnetic bearing to cause the impeller to move until a bearing power indicator indicative of the power used by the magnetic bearing reaches the reference power.

In one broad form, one aspect of the present invention seeks to provide a heart pump including: a housing defining a cavity including at least one inlet and at least one outlet; an impeller provided within the cavity, the impeller including vanes for urging fluid from the inlet to the outlet upon rotation of the impeller; a drive that rotates the impeller within the cavity; a magnetic bearing including at least one bearing coil that controls an axial position of the impeller within the cavity; and, a controller including an electronic processing device that: determines an impeller indicator indicative of operation of the impeller within the cavity; determines a reference power in accordance with the determined impeller indicator; and, controls the magnetic bearing to cause the impeller to move until a bearing power indicator indicative of the power used by the magnetic bearing reaches the reference power.

In one embodiment the impeller indicator is indicative of at least one of: an axial position of an impeller within the cavity; and, a rotational speed of the impeller within the cavity.

In one broad form, one aspect of the present invention seeks to provide a controller for a heart pump, the controller including an electronic processing device that: determines an impeller indicator indicative of operation of an impeller within a cavity; determines a reference power in accordance with the determined impeller indicator; and, controls a magnetic bearing to cause the impeller to move until a bearing power indicator indicative of the power used by the magnetic bearing reaches the reference power.

In one broad form, one aspect of the present invention seeks to provide a method for controlling a heart pump, the method including, in an electronic processing device: determining an impeller indicator indicative of operation of an impeller within a cavity; determining a reference power in accordance with the determined impeller indicator; and, controlling a magnetic bearing to cause the impeller to move until a bearing power indicator indicative of the power used by the magnetic bearing reaches the reference power.

It will be appreciated that the broad forms of the invention and their respective features can be used in conjunction and/or independently, and reference to separate broad forms in not intended to be limiting.

BRIEF DESCRIPTION OF THE DRAWINGS

Various examples and embodiments of the present invention will now be described with reference to the accompanying drawings, in which.

DETAILED DESCRIPTION OF THE PREFERRED EMBODIMENTS

Figure 1A:
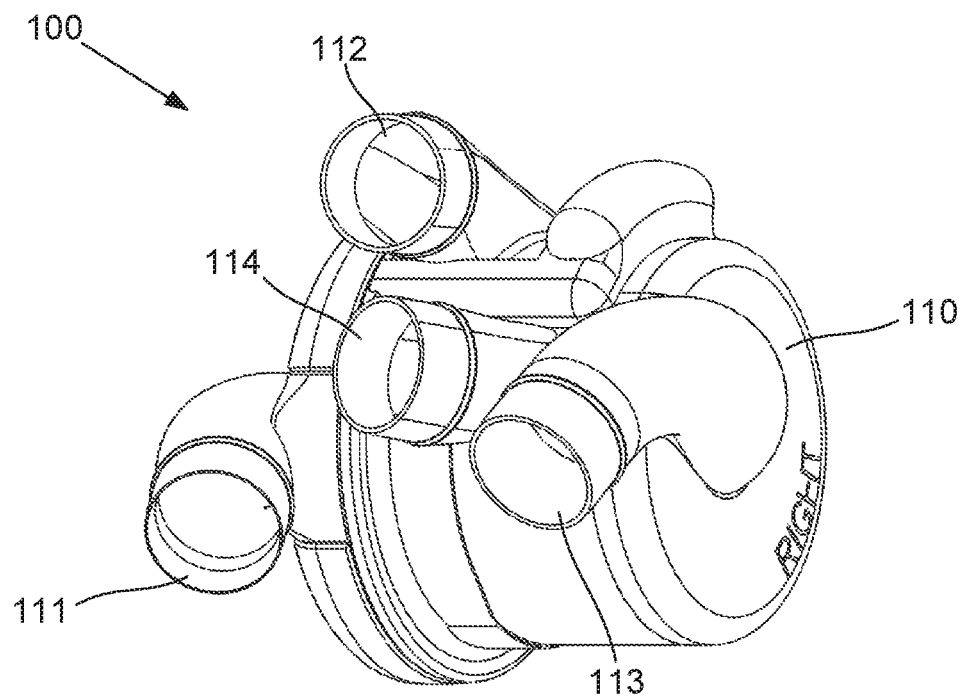
FIG. 1A is a schematic perspective view of an example of a heart pump.

An example of a heart pump will now be described with reference to FIGS. 1A to 1D.

In this example the heart pump is a biventricular device, which can operate either as a ventricular assist device to assist function of left and right ventricles of a subject's heart, or alternatively as a total artificial heart. It will be appreciated however that whilst reference is made to a biventricular device this is not essential, and alternatively the control processes described herein could equally be applied to single ventricular assist devices or any other form of blood pump.

In this example, the heart pump 100 includes a housing 110 defining a cavity 115. The housing can be of any suitable form but typically includes a main body 110.1, left and right end caps 110.2, 110.3 which connect to the main body 110.1, as well as an end plate 110.4 positioned between the main body 110.1 and left end cap 110.2. The housing can be made of any suitable biocompatible material, and can be made of titanium, a polymer or the like.

The housing 110 includes two inlets 111, 113, for connection to the left atrium/pulmonary vein and right atrium/vena cava, or left and right ventricles, and two outlets 112, 114 for connection to the aorta and pulmonary artery, respectively. Whilst two inlets and outlets are shown, it will be appreciated that this is in the context of a biventricular device, and that a single inlet and outlet can be used for a single ventricular device.

The heart pump 100 includes an impeller 120 provided within the cavity 115. The impeller 120 includes a rotor 121 having vanes mounted thereon for urging fluid from the inlet to the outlet upon rotation of the impeller 120. In this example, as the heart pump 100 is a biventricular device, the impeller includes two sets of vanes 122, 123 each of which is used for urging fluid from a respective inlet 111, 113 to a respective outlet 112, 114. In this example, the rotor 121 is positioned within the cavity 115 to effectively divide the cavity into first and second cavity portions, each having a respective inlet and outlet, thereby allowing each to function as a respective pump.

Figure 1B:
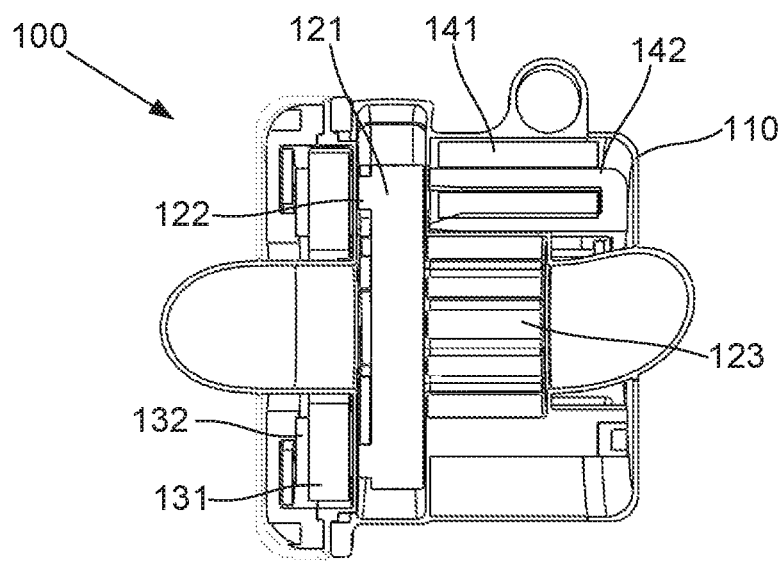
FIG. 1B is a schematic cutaway view of the heart pump of FIG. 1A.
Figure 1C:
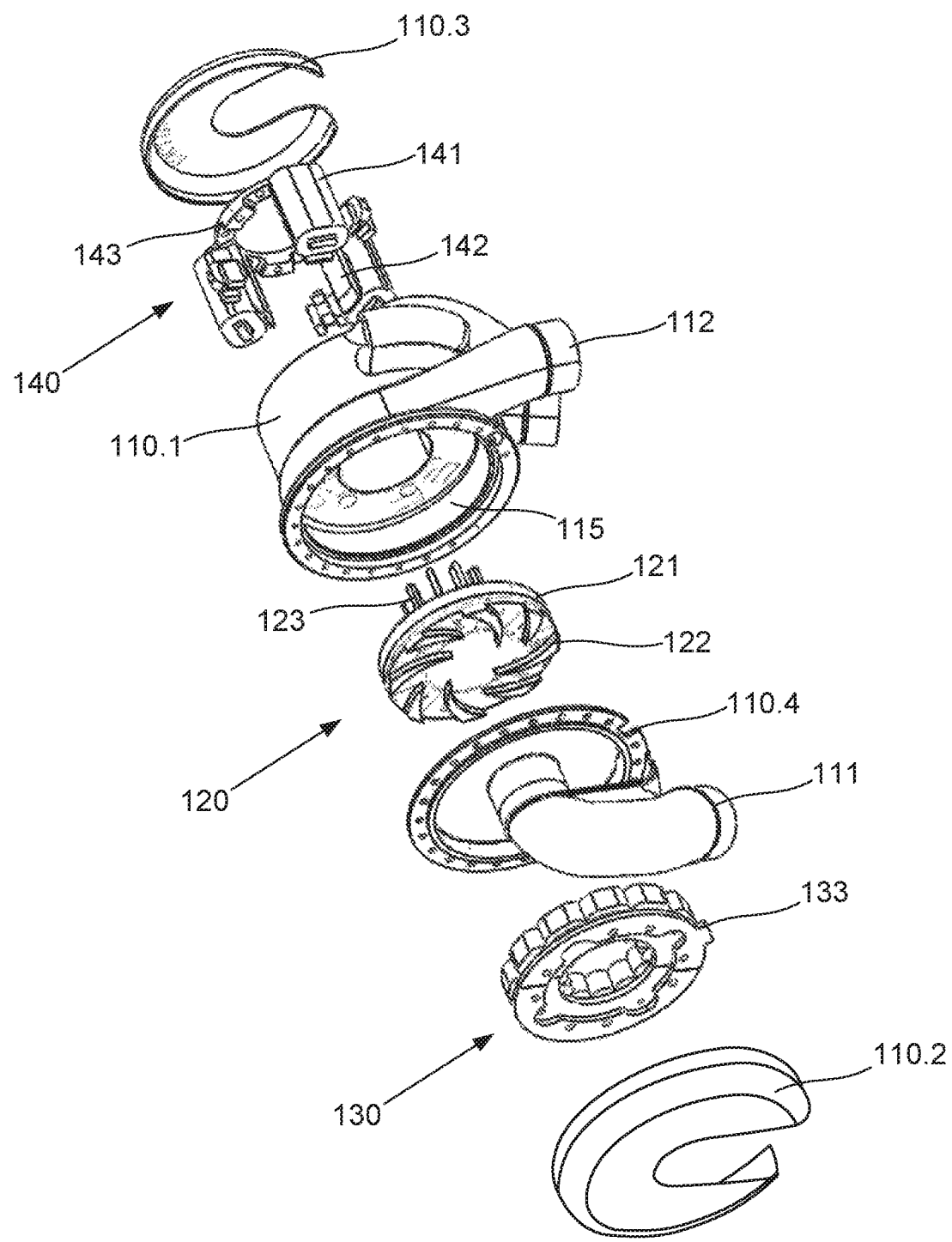
FIG. 1C is a schematic perspective exploded view of the heart pump of FIG. 1A.

Thus, in the current example, the vanes 122 are used to urge fluid from the inlet 111 to the outlet 112, with this being provided on the left-hand side of the pump in the orientation shown in FIG. 1B, and operating to provide left-ventricular function, whilst the vanes 123 urge fluid from the inlet 113 to the outlet 114 and act to provide right-ventricular function. In this context the first and second cavity portions are generally referred to as left and right cavities, respectively. It will be appreciated that in this regard, the terms left and right refer to the intended ventricular function of the cavities as opposed to the particular orientation of the pump in FIG. 1B, which is used for illustrative purposes only.

The heart pump 100 further includes a drive 130 that rotates the impeller 120 within the cavity 115. The drive 130 can be of any appropriate form but typically includes a number of coils 131 wound on a stator 132, supported by a mounting 133, allowing the drive 130 to be coupled to the housing 110. The drive cooperates with magnetic material 134 mounted in the rotor 121 with this typically being in the form of a number of circumferentially spaced permanent magnets mounted in the rotor 121 proximate an outer circumferential edge of the rotor and proximate a face of the rotor facing the drive coils 131. In one specific example, the coils 131 and stators 132 are wedge shaped and circumferentially spaced around the mounting 133, so as to provide twelve electromagnets radially aligned with circumferentially spaced drive magnets 134 in the rotor 121, to thereby maximise a degree of magnetic coupling between the magnets in the rotor 121 and the drive 130. The drive magnets 134 are typically arcuate shaped rare earth magnets, circumferentially spaced proximate an outer circumferential edge of the rotor 121, and mounted on a soft iron rotor drive yoke.

The heart pump 100 can further include a magnetic bearing 140 including at least one bearing coil 141 which cooperates with bearing magnetic material mounted in the rotor 121 to thereby control an axial position of the impeller 120 within the cavity 115. In one particular example, shown in more detail in FIGS. 2D to 2F, the magnetic bearing includes three bearing coils 141, each of which is mounted on a first leg 142.1 of respective U-shaped stators 142, with a second leg 142.2 being positioned radially inwardly of the first leg 142.1. The stators 142 are mounted to a support 143 and circumferentially spaced 120° apart around the housing so that the first and second legs 1421. 142.2 align with respective bearing magnetic material, such as bearing magnets 144, 145, optionally mounted on a common yoke (not shown) allowing an axial position of the impeller 120 to be controlled.

The bearing magnetic material typically includes first and second annular magnetic bearing members mounted within and proximate a face of the rotor facing the bearing coils 141, the first magnetic bearing member being provided radially outwardly of the second magnetic bearing member. In one particular example, the first bearing magnet material 144 includes an annular soft iron material that can be integrally formed with the annular yoke, or an annular permanent magnet 144 mounted on the yoke, and mounted in the rotor, proximate an outer circumferential edge of the rotor 121. The second bearing magnetic material is an annular permanent bearing magnet 145 mounted radially inwardly of the first bearing member 144, so that the first and second bearing members 144, 145 align with respective legs 142.1, 142.2 of the stators 142. It will be appreciated the annular members could include a plurality of individual elements, such as individual circumferentially spaced magnets or ferromagnetic elements. Additionally, the use of a magnetic bearing may not be required and can be replaced by a static physical bearing, or the like.

The drive 130 and magnetic bearing 140 are mounted at opposing ends of the housing 110 so that the drive and bearing 130, 140 are provided proximate opposing surfaces of the rotor 121 as shown for example in FIG. 1D, and FIGS. 2G, 2H, 2J and 2K. In the current example the drive 130 is mounted adjacent the left pump, whilst the bearing 140 is mounted adjacent the right pump, although the opposite configuration is contemplated. The depicted arrangement has a number of benefits.

Firstly, the inherent attractive magnetic forces between the drive and rotor and the bearing and rotor can be configured to substantially balance when the rotor is provided at a balance point at a normal operating speed, which may for example by approximately at a center of the cavity under conditions of normal flow.

For example, this arrangement can be configured so that the magnetic forces inherent between the drive 130 and impeller 120, and between the magnetic bearing 140 and impeller 120 are matched at an impeller balance position within the cavity, which corresponds to a desired position of the impeller under conditions of normal flow. This minimises the bearing current required to maintain the position of the impeller 120 within the cavity, hence reducing the amount power required to operate, and in particular drive and axially position the impeller.

Additionally, as well as having the magnetic forces balance, the forces generated by the drive and bearing can also be configured to provide a desired degree of axial and radial stiffness. In this regard, the stiffness is a measure of the deflection of the impeller 120 from a balance position in response to an external force. In one example, it is desirable to maximise the radial stiffness so as to maintain the impeller radially centralised within the cavity and to stop the impeller touching the inner circumferential wall of the cavity. Conversely, as the axial position of the impeller 120 can be used for flow control, and in particular to allow for passive and/or active response to changes in hemodynamic parameters, a low degree of axial stiffness is preferred. Accordingly, the passive magnetic forces can be configured to assist in meeting these requirements, as will be described in more detail below.

A further benefit of the above described arrangement, in the context of BiVAD applications, is that it allows the greater size of the magnetic bearing to be accommodated by the smaller size of the right pump cavity. In particular, this allows a gap between a bearing stator and bearing magnets to be minimized, as no vanes are located in this gap (as opposed to the left side where vanes are located in the magnetic airgap between the drive and the rotor), as will be described in more detail below. However, it will be appreciated that this limits an outer diameter of the right pump and thus achievable pressure generation at a given rotational speed, although for right pumps this is generally not an issue given their lower flow requirements than the left pump.

The apparatus further includes a controller 150 which, in use, is coupled to a sensor 160 and the drive and bearing coils 131, 141. The sensor 160 senses an axial position of the impeller 120 within the cavity 115 and can be of appropriate form such as a reluctance or eddy current sensor, which detect magnetic fields within the rotor 121 to thereby determine a separation between the rotor and the sensor 160, as will be appreciated by persons skilled in the art.

Typically three sensors would be provided circumferentially spaced around the rotor. In the case of eddy current sensors 160, each sensor would typically include a coil mounted in a housing, circumferentially spaced and aligned with the inner leg 142.2 of the magnetic bearing stators 142. The coil is aligned with a rotor shell/target mounted radially inwardly of a first bearing magnet 144, so as to generate a field therein, with variations in the field being detected to determine the separation of the sensor 160 and the shell/target, and hence the rotor 121. However, it will be appreciated that other suitable sensors can be used, such as reluctance sensors or the like, in which case the first permanent magnet 144 might be replaced with ferromagnetic material, depending on the sensor/bearing requirements.

In use the controller 150 is adapted to monitor signals from the position sensor 160 and then control the current supplied to the drive coils 131 to control rotation of the impeller and to the bearing coils 141 to control the axial position of the impeller 120.

The controller 150 can be of any suitable form but typically includes an electronic processing device 151, an optional memory 152, and an interface 154 for connecting to the heart pump, each of which are interconnected by a bus 155, or other similar arrangement. The electronic processing device can be any form of electronic processing device capable of interpreting signals and causing the drive and bearing to be controlled, such as a microprocessor, microchip processor, logic gate configuration, firmware optionally associated with implementing logic such as an FPGA (Field Programmable Gate Array), or any other electronic device, system or arrangement.

An optional external interface 153 may be provided allowing for interaction with the controller 150. In the event that the controller is positioned outside the body this could include an I/O device 153 such as a touch screen or the like, whereas if positioned inside the body this would typically be in the form of a wireless communications module allowing communication with an external control device.

Figure 1D:
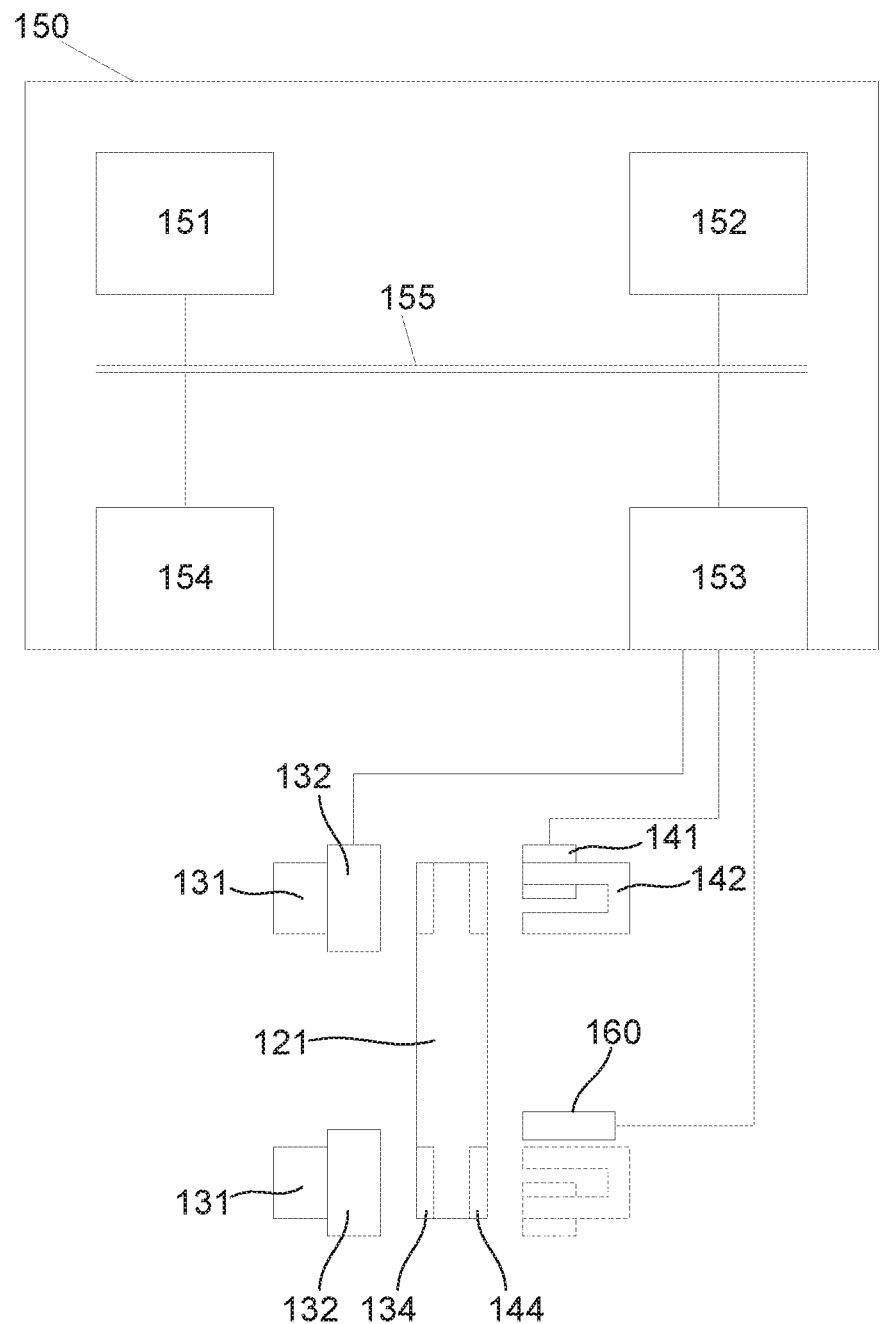
FIG. 1D is a schematic diagram of an example of a control system for the heart pump of FIG. 1A.
Figure 2:
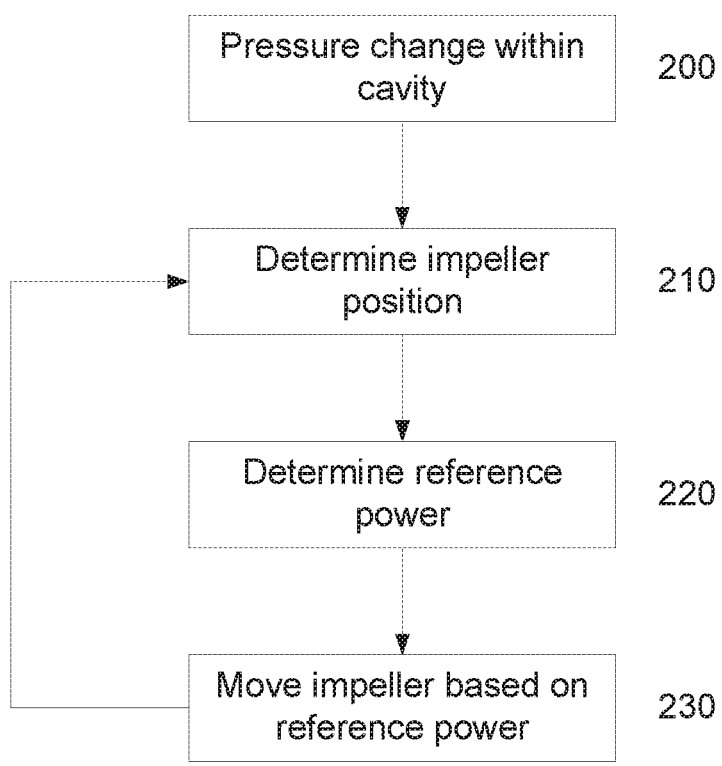
FIG. 2 is a flowchart of an example of a control process for controlling an axial position of an impeller.
Figure 3:
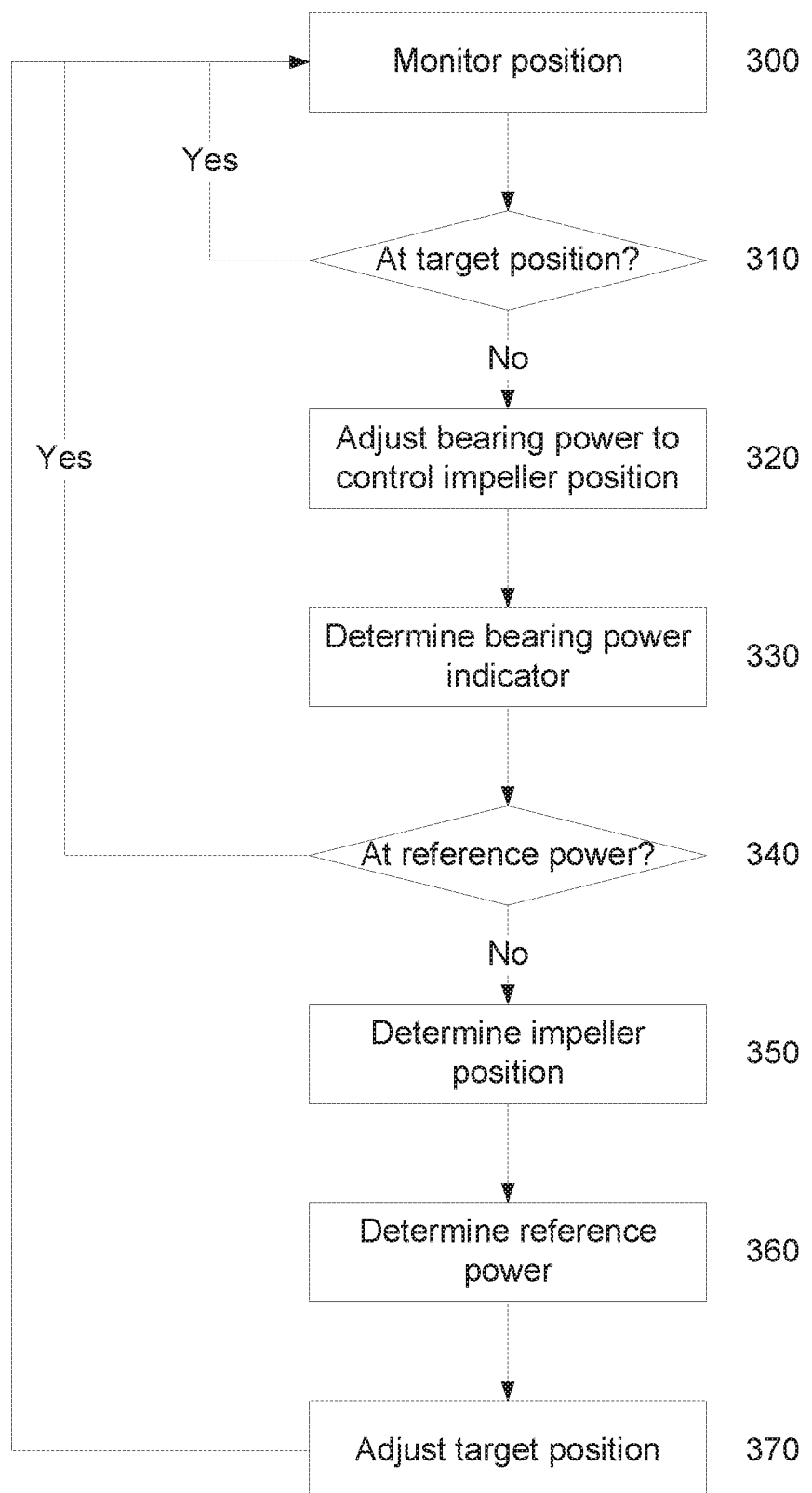
FIG. 3 is a flowchart of a specific example of a process for controlling an axial position of an impeller.

Operation of the control system 150 of FIG. 1D will now be described with reference to FIG. 2.

In this example, when operating under normal conditions, the impeller 120 is magnetically suspended within the cavity 115, with hydraulic forces acting on the impeller 120 due to fluid pressure within each of the left and right cavities and magnetic forces generated by the drive 130 and bearing 140 being substantially balanced. In this instance the impeller 120 is typically suspended at a reference position within the cavity, sometimes referred to as a central position.

At step 200, a pressure change occurs within one or both of the left or right cavities. The pressure change would typically occur as a result of a physiological change within the subject which could arise for any one of a number of reasons, such as the subject moving, commencing exercise, or the like. The pressure change will generally result in a change in the hydraulic forces acting on the impeller 120 resulting in a net force towards the left or right cavity for the current bearing settings.

At step 210, the controller 150 determines the axial position of the impeller 120, and uses this to determine a reference power at step 220. In particular, the reference power is defined as a function of impeller position, with the reference power varying based on a distance of the impeller from the notional central position with the cavity.

At step 230, the controller 150 moves the impeller by controlling the magnetic bearing 140 to cause the impeller 120 to move until a bearing power indicator indicative of the power used by the magnetic bearing reaches the reference power.

The bearing power indicator can be of any appropriate form, but in one example is indicative of or derived from the bearing current drawn by the magnetic bearing, for example based on a filtered version of the raw current signals, with the reference power corresponding to a respective current value. However, it will be appreciated that this is not essential, and any suitable bearing power indicator and corresponding type of reference values can be used.

In the above process, when moving the impeller this typically involves moving the impeller in a direction opposite the direction of the net force on the impeller 120, so that for example if the net force is acting towards the right cavity, for example due to an increase in pressure in the left cavity, the magnetic bearing 140 is controlled to cause the impeller 120 towards the left cavity. This movement brings the impeller 120 towards the drive 130, thereby increasing attractive forces between the drive 130 and impeller 120, while reducing attractive forces between the bearing 140 and impeller 120, which in turn helps counteract the hydraulic forces, reducing the bearing current required to maintain the impeller at a balance position.

It will be appreciated that this is broadly similar to the "zero-power" controller configuration described for example in U.S. Pat. No. 8,636,638. However, in contrast to the technique described therein, in which a constant and typically minimal reference power is used, the reference power is defined as a function of the axial position of the impeller within the cavity. Accordingly, as the impeller moves within the cavity, the controller 150 repeats steps 210 to 230, determining a new reference power based on the new axial position of the impeller 120, using this to control further movement of the impeller 120.

In one example, the reference power determined by the controller increases as the impeller 120 moves away from the notational centre point within the cavity. The effect of this is that when compared to a traditional zero-power control process, additional movement of the impeller is induced. Thus, in this example, when moving the impeller towards the left cavity, the further movement will typically include moving the impeller further towards the left cavity, in effect amplifying the movement induced by the zero-power control approach.

The reason for performing additional movement control is to amplify changes in fluid flow between the inlet(s) and outlet(s). In this regard, movement of the impeller has an impact on the efficiency of the pump, with a reduction in separation between the vanes 122, 123 and cavity leading to an increase in pump efficiency. Accordingly, moving the impeller 120 within the cavity 115 can be used to increase or decrease pump flow.

In the case of a single ventricular device moving the impeller can be used to increase or decrease flow. In a biventricular device however, this can increase/decrease one pump output, whilst simultaneously decreasing/increasing the other pump output, which is particularly useful in balancing fluid pressures between the left and right cavities, and hence within the systemic and pulmonary circulatory systems in the subject. For example, a decrease in left-ventricular pressure requires an increase in blood flow through the left ventricle in order to return pressure to normal levels. Accordingly, this can be achieved by moving the impeller towards the left cavity, increasing the effectiveness of left ventricular function.

It will be appreciated from the above that a greater movement of the impeller will result in a higher increase in efficiency of the pump and hence a higher fluid flow, which in turn returns pressures to a balanced condition more effectively. As a result, there is a desire to effectively maximise the degree of movement for any particular change in pressures and hence hydraulic forces within the pump.

In this regard, the degree of axial movement of the impeller 120 within the cavity 115 will naturally vary depending on the axial stiffness of the magnetic bearing arrangement. In particular, a relatively weak stiffness will result in a higher degree of axial movement for a given pressure change, which in turn can enhance the effectiveness of the ability of the heart pump to correct pressure imbalances, for example between the left and right sides. Conversely, a magnetic bearing with a high degree of stiffness will result in a relatively small amount of axial movement for a given pressure change, meaning the effectiveness to correct pressure imbalances in reduced.

From this, it will be appreciated that one option to maximise movement of the impeller, and hence the effectiveness of the pump to correct imbalances is to use an axially weak magnetic bearing. However, the axial stiffness of the magnetic bearing is dependent on the degree of magnetic coupling between the bearing 140 and impeller 120, which in turn also affects the radial stiffness, meaning an axially weak magnetic bearing is also radially weak, which in turn allows for radial movement of the impeller within the cavity. Such radial movement is undesirable as this can lead to contact between the rotor 121 and an inner wall of the cavity 115, which can cause damage to the pump. Additionally, even if contact does not occur, a small separation between the rotor 121 and cavity wall can lead to high shear stresses, which in turn can case rupturing of blood platelets leading to hemolysis.

Accordingly, in one example it is desirable to provide a magnetic bearing that has significant radial stiffness, so as to restrict radial movement of the impeller, but which at least mimics the effect of an axially weak bearing. This can be achieved through the utilisation of the above described control process which uses a physically strong axial magnetic bearing, and hence a radially strong bearing, but implements additional control processes in order to simulate the effect of an axially weak bearing. This assists in providing a magnetic bearing that allows the pump to respond to pressure changes within the cavities to balance flows, whilst preventing radial movement of the impeller. However, it will be appreciated that the techniques described herein can be conversely used to increase the effective axial stiffness, which can be used to avoid the impeller reaching an extreme axial position within the cavity, as will be described in more detail below.

A number of further features will now be described.

As previously mentioned, the control process operates to move the impeller in a direction opposite a net force induced on the impeller. Accordingly, when the change in hydraulic forces generates a resultant force acting on the impeller in a first axial direction, the controller controls the magnetic bearing to move the impeller in the second axial direction opposite to the first axial direction. Thus, an increase in pressure in the left cavity will cause the impeller to be moved towards the left cavity.

The controller 150 can determine changes in axial hydraulic forces within the cavity either by detecting axial movement of the impeller within the cavity, for example by detecting movement in the first direction, or by detecting changes in the bearing power indicator required to maintain the impeller at a constant axial position within the cavity. The technique used will vary depending upon the preferred control implementation. In particular, in one example, the controller 150 can implement a bearing control process which operates to adjust the power used by the magnetic bearing 140 in order to maintain the impeller 120 at a constant position, in which case changes in bearing power will be used to determine the net forces, whereas alternatively the controller 140 could attempt to maintain a constant power, in which case movement of the impeller 120 would be detected.

In one example, the controller determines changes in axial hydraulic forces by filtering a bearing current signal using a low pass filter. The low pass filter can have a cut-off of at least one of: between 0.1-10 Hz, between 1-15 Hz; between 15-30 Hz; approximately 15 Hz; approximately 30 Hz; approximately 1 Hz; and, between 30-100 Hz.

Typically the controller 150 operates to iteratively move the impeller 120 by repeatedly controlling the magnetic bearing to move the impeller 120 to a new axial position in accordance with the reference power, then modifying the reference power in accordance with the new axial position of the impeller. This process can be repeated until a desired end point is reached. This can be performed on the basis of a set number of iterations but more typically is performed until the modified reference power reaches a defined threshold value, the axial position reaches a defined threshold or the hydraulic forces are either balanced or overcome. Thus, it will be appreciated that this process can continue until the impeller 120 reaches a maximum extreme position within the cavity 115, for example corresponding to a distance of minimum separation from the cavity wall, or until the hydraulic forces are again balanced.

In one particular example, the operating range of the impeller is restricted to +/−200 μm when operating in a total 0.6 mm clearance, so as to not allow the impeller to come with 100 μm of the stationary housing to assist with hemocompatibility. However the rotor may be able to come within 50 μm of the stationary casing at critical times to assist with flow balancing, effectively expanding the range of movement to +/−250 μm. It would be appreciated that these limits from the housing are fixed, resulting in a larger operating range as total clearance gap increases.

In one example, it can be desirable to operate the bearing so that the impeller does not reach an axial position limit, for example to accommodate changes in impeller rotational speed, which can in turn impact on the magnetic forces generated by the drive. For example, if the impeller reaches an axial position limit, the impeller can't move any further so additional changes in forces acting on the impeller must be counteracted solely by changes in the magnetic forces generated by the bearing and hence the bearing current used, and not the usual control of changes in bearing current and impeller position. This can lead to excessive changes in bearing current, which can in turn impact on other control processes, such as the detection of characteristic force events or control of impeller rotational speed, described for example in application U.S. Ser. No. 62/275,723, the contents of which are incorporated herein by cross-reference.

Accordingly, in one example, the above described control process can be used to alter the effective stiffness of the system different for different regions of the operational range. For example, as the impeller gets closer to a positional limit, the controller can be used to increase the effective axial stiffness of the bearing, which would mean that a further increase of the forces would result in a smaller axial movement.

In one example, the system can have a dynamic effective axial stiffness based on the impeller position, so that in a central region of the cavity, the impeller can have a low axial stiffness to provide maximum axial and hence hemodynamic responsiveness. Conversely, towards limits of axial position, the stiffness can be increased to thereby reduce the axial responsiveness, thereby avoiding the impeller passing beyond limits and impacting on the housing, whilst also reducing the likelihood of current peaks or spikes impacting on other control algorithms or resulting in excess power use.

It will also be appreciated that the impeller position can be controlled on the basis of a first limit and a second limit, with the first limit defining a preferred impeller position range and the second limit defining a maximum impeller position range. In this regard, the first limit can provide a soft limit, which is a notionally preferred limit to the axial position, as compared to a hard limit defined by the second limit, which is an axial position beyond which there is a risk of the impeller contacting the housing.

The controller 150 typically determines the reference power by progressively increasing a magnitude of the reference power by a progressively smaller amount for each iteration, such that the degree of movement reduces on each iteration as the impeller 120 moves away from the zero-power reference position. This allows the impeller to be moved asymptotically towards a new balance position, in particular allowing for initial rapid coarse correction, with fine correction being implemented as the impeller reaches a new balance position. However, any function relating the reference power to the axial position of the impeller within the housing can be used, for example to reduce the amount of movement when compared to the traditional zero power configuration, thereby providing a bearing that is effectively axially stiffer.

In one example, the controller 150 controls the magnetic bearing to cause the impeller 120 to move to a target axial position. The controller 150 then determines if the bearing power indicator is at the reference power at the target position, and if not, determines a new target axial position of the impeller, determines a reference power in accordance with the new axial position and uses the reference power to determine a new target axial position. This process can then be repeated providing a positive feedback loop, until such time as the bearing power indicator reaches the reference power, when at the current defined target position.

In one example, the controller 150 includes a bearing controller that uses signals from the position sensor 160 to determine the current axial position of the impeller 120, controls the current supplied to the magnetic bearing to thereby maintain the impeller 120 at a target axial position and outputs an indication of the bearing power indicator and current axial position. The controller 150 then further includes a position controller that uses the bearing power indicator and current axial position to determine a target axial position which is then provided to the bearing controller. In this regard, the bearing and position controllers could include physically separate hardware, but more typically are logically separate control processes implemented on a common processing device, as will be described in more detail below.

Furthermore, the position controller can include a first controller that calculates a reference power using the current axial position of the impeller and a second controller that determines the target axial position using the reference power and the bearing power indicator. Additional details of the control arrangement will be described in more detail below.

The controller 150 can also operate to record an indication of the bearing power indicator and such or the current axial position allowing this to be reviewed, for example for logging purposes.

Accordingly, the above described processes allow a heart pump to be implemented with a magnetic bearing system having a high degree of axial stiffness, whilst maintaining a degree of control over flow balance typically only achievable with a low stiffness bearing configuration.

A further example control process will now be described with reference to FIG. 3 and FIGS. 4A to 4D. For the purpose of this example, bearing current is used as an indicator of bearing power, but it will be appreciated that this is not intended to be limiting in the context of the application as a whole.

Figures 4A, 4B:
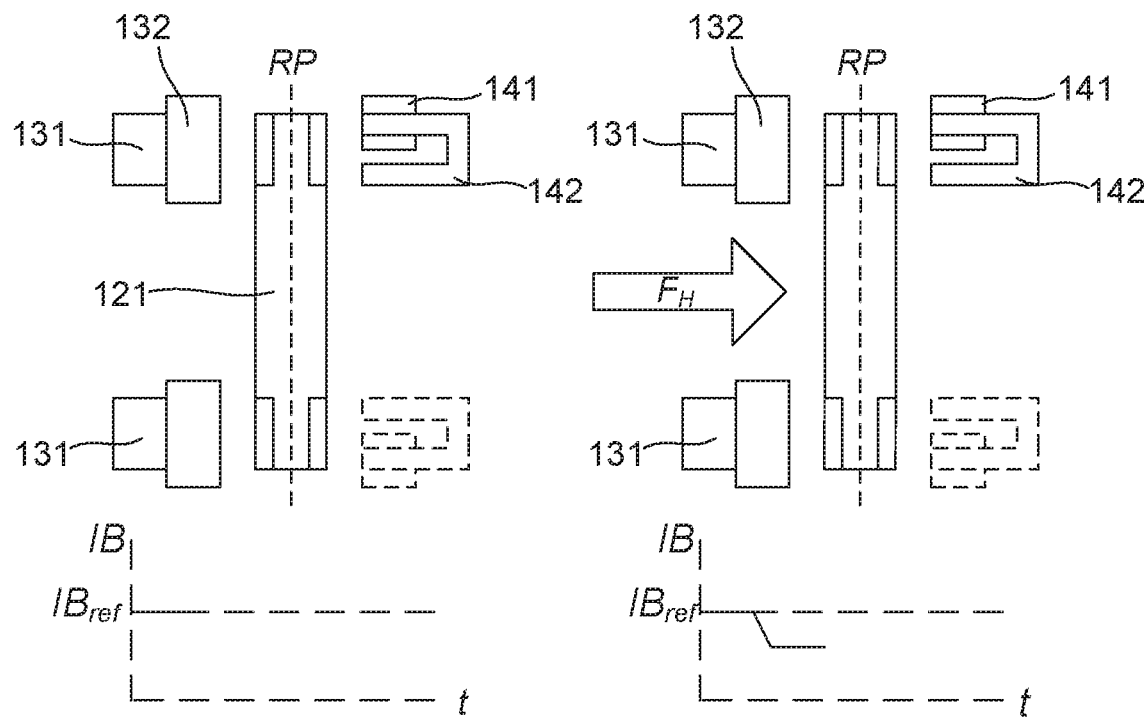
FIGS. 4A to 4D are schematic diagrams illustrating an axial position of an impeller under varying conditions.

In this example, at step 300, the controller 150 monitors a position sensor 160 and determines if the impeller 120 is at a target position at step 310. Under nominal flow conditions (referred to as balanced conditions), the impeller 120 is provided at an initial reference position RP, with the bearing current IB remaining substantially constant at a reference level $IB_{ref}$, as shown in FIG. 4A. If there is no impeller movement, and the impeller is at the target position, the process returns to step 300, allowing the position to be monitored in an ongoing process.

Assuming there is impeller movement, the controller 150 will adjust the bearing power to maintain the impeller 120 at the target impeller position, initially corresponding to the reference position RP. In the example of FIG. 4B, an increase in left ventricular pressure leads to a net hydraulic force towards the right cavity, as shown by the arrow $F_H$, which initially causes movement of the impeller to the right cavity. Accordingly, the controller 150 adjusts the current used by the magnetic bearing, reducing the attractive force between the impeller 120 and bearing 140, so as to counteract the hydraulic force $F_H$. In this regard, it will be appreciated, that this may involve reducing the magnitude of the applied bearing current, or applying a negative bearing current to repel the impeller 120 from the bearing, depending on the magnitude of the reference current $IB_{ref}$. It should be noted that the term reference current $IB_{ref}$ is effectively equivalent to the reference power, and these two terms should be considered as interchangable.

Steps 300 to 320 are typically performed by on a continuous basis so as to maintain the impeller at a defined target position within the cavity.

At step 330, the controller 150 determines the bearing power indicator in the form of the bearing current IB and determines if this is equal to the reference power $IB_{ref}$ at step 340. If not, at step 350, the controller 150 determines the position of the impeller 120, with this being used to determine a reference power at step 360, which is in turn used to determine a new target position.

Figures 4C, 4D:
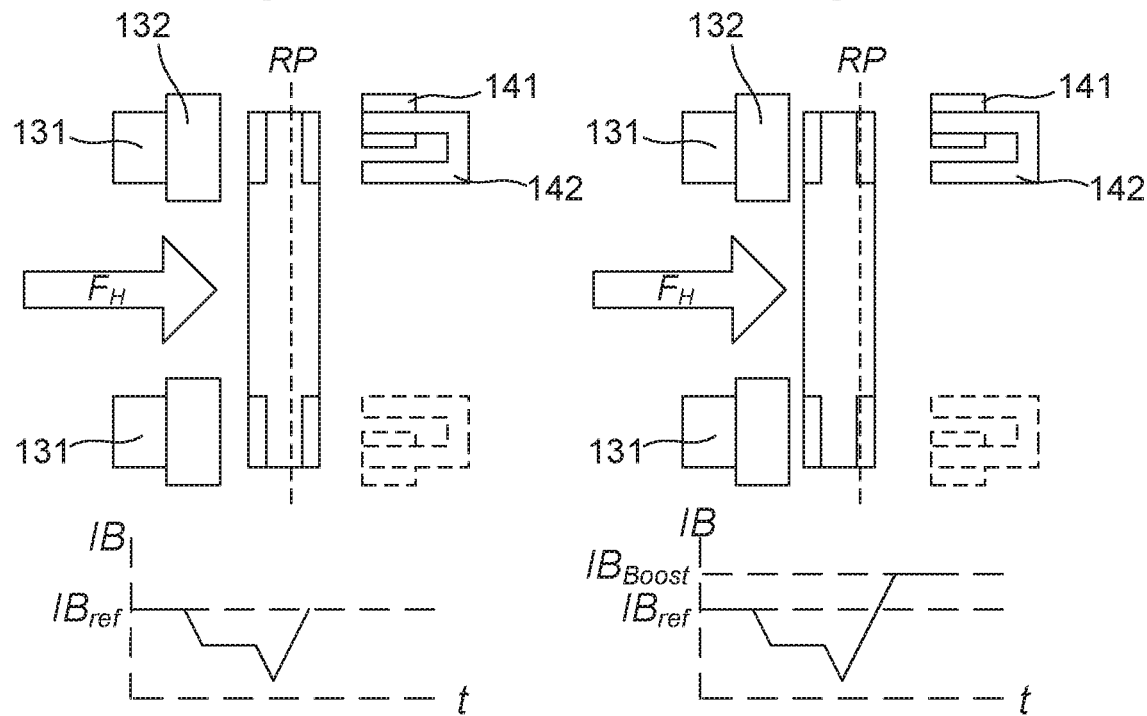

In this instance, initially the impeller is provided at the initial reference position RP, which is generally at a notional centre of the cavity, and accordingly the reference power is $IB_{ref}$, which results in the impeller moving towards a target position located in the left cavity. This is achieved by initially reducing the magnitude of the applied bearing current IB, or applying a negative bearing current to repel the impeller 120 from the bearing 140, until the impeller reaches the target position, as shown in FIG. 4C. In the previous zero-power approaches, the impeller would halt at the position once the bearing power reaches the reference power $IB_{ref}$.

However, in the current example, as the impeller moves towards the target position shown in FIG. 4C, the controller 150 repeats the process of steps 340 to 370, progressively adjusting the reference power as the impeller 120 moves. In this example, the target position of the impeller is progressively adjusted until the impeller reaches a target position in which the bearing power indicator is equal to a boosted reference power $IB_{Boost}$, shown in FIG. 4D. Thus it will be appreciated that the modified zero-power control approach causes the impeller 120 to be moved further into the left cavity.

Accordingly, in the above described arrangement, the magnetic bearing system has a dual purpose: namely levitating the rotor and maintaining axial and radial stability, as well as enabling axial rotor translation to provide flow control, and in particular differential flow control in the case of a biventricular assist device. To maintain stability, the bearing system is preferably "stiff", so that a small radial or axial movement results from disturbing physical forces created by the motor's magnetic field, or the patient's movement act on the rotor. In contrast, for flow control the axial bearing needs to be "soft", so that a change in left or right atrial pressure shall result in a large axial rotor movement to balance left and right outflows.

The system's stiffness is determined by the mechanical and electrical design of the device, and in particular the drive and bearing design, so this needs to be determined during the design phase. However, implementing an axially stiff bearing may not fully utilize the available impeller movement range within the cavity of the device, when encountering disturbance forces created by variations in inflow and outflow pressures. Therefore, it may be desired to attain an "overreaction", in which greater impeller movement is performed. By implementing the above described control processes, this allows a physically stiff bearing to function in a manner similar to that of an axially soft bearing, allowing the benefits of both stiff and soft bearings to be achieved.

Figure 5A:
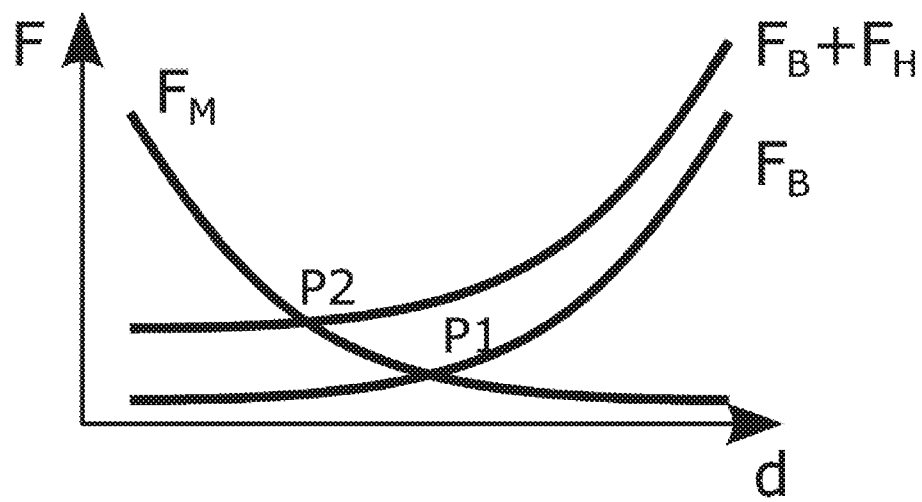
FIG. 5A is a graph illustrating magnetic force distribution on a magnetically levitated impeller.

As previously described, in the current arrangement, the impeller is axially suspended by two magnetic fields, created by the drive 130 on the left and the bearing 140 on the right. Each field creates a force $F_M$ and $F_B$ that acts on the impeller, with examples of the forces being shown in FIG. 5A.

In this example, the displacement d is counted positive towards the right cavity, with the point P1 corresponding to a balanced position in which the drive and magnetic bearing forces are equalized. The steeper the force curves, the higher the absolute system stiffness |F/d| and the better axial and radial stability. The impeller is maintained in position by an active controller system, so to reduce the energy consumption, a portion of the bearing force $F_B$ is created by permanent magnets so that less or no current in the bearing coils is required to maintain the position.

In order to adjust the impeller position, the coils are energized with a bias current $IB_{Ref}$. A typical bearing current IB versus displacement curve $IB_{FB}$ is plotted in FIG. 5B. Adding a positive current moves the rotor towards the left cavity, whilst a negative current would move the rotor towards the right cavity.

When the bearing system is operated in zero-power mode, the controller seeks to minimize IB to zero, so that $F_B$ is solely created by the permanent magnets. With the zero-power mode activated, a hydraulic force $F_H$ on the rotor in axial direction will move it opposite to the force's direction. Thus, in FIG. 5A, $F_H$ acts towards the right, which increases the total force $F_B+F_H$ towards the right cavity. If the impeller position were maintained, a bearing current IB would be required in order to reduce the bearing force $F_B$. However, the zero-power controller aims to minimize IB, which is achieved by moving the impeller towards the left cavity, to the new point of equalized forces, point P2, where IB is minimal.

Figure 5B:
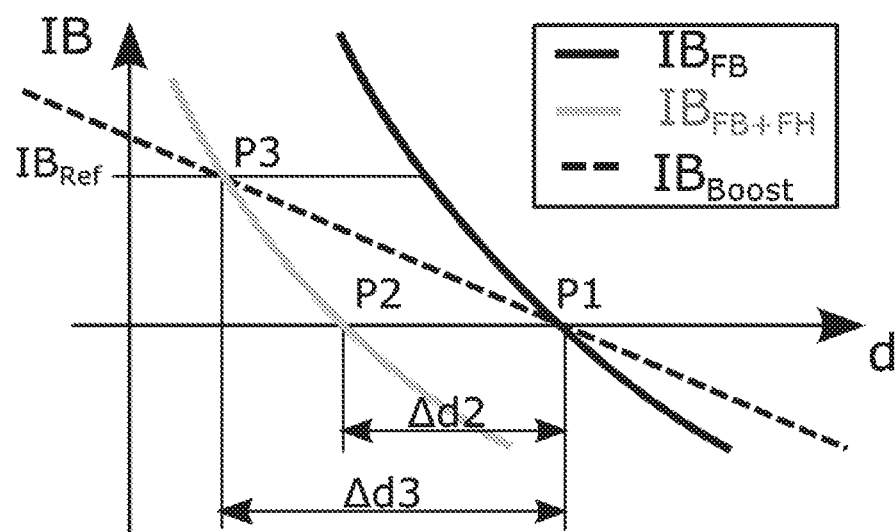
FIG. 5B is a graph illustrating a relationship between bearing current and displacement under a variety of operating conditions.

In FIG. 5B, the result of the additional force can be observed as a shift of bearing current $IB_{FB}$ towards the left, as shown by curve $IB_{FB+FH}$. The impeller moves by the distance Δd2. In order to allow for a rotor position adjustment, while under zero-power control, a non-zero value for $IB_{Ref}$ can be selected. For the purpose of responding to changes in the hydraulic forces with an appropriate rotor movement, the stiffness $F_H/Δd2$ is required to be low.

Thus, the fundamental control strategy of a zero-power controller is to minimize power consumption of the magnetic bearing system by reducing the average bearing current to zero.

The arrangement described above builds on the pre-existing zero-power system, manipulating $IB_{Ref}$ by adding a booster current $IB_{Boost}$, the additional current $IB_{Boost}$ is selected depending on the current impeller position, as shown by the dashed line in FIG. 5B, resulting in the impeller moving by the distance Δd3 to the position P3. By this means a feedback loop is created that allows to amplify the impeller movement for given hydraulic forces, thereby simulating a lower stiffness.

Figure 5C:
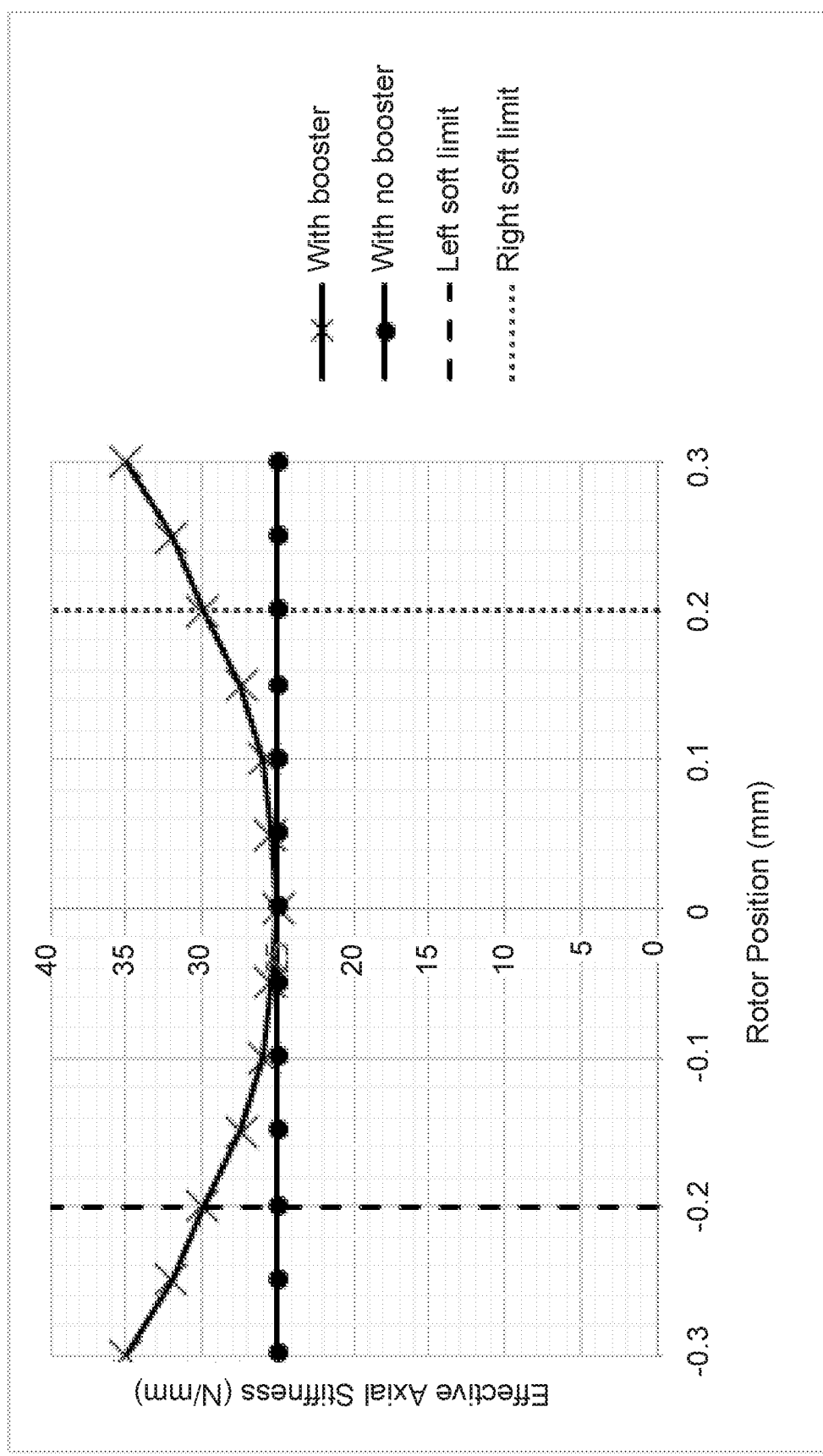
FIG. 5C is a graph illustrating a relationship between axial stiffness and impeller axial position.

As also previously mentioned, it can be desirable to have a dynamic stiffness that adjusts based on the impeller position. An example of this is shown in FIG. 5C. In this example, the effective axial stiffness is shown in N/mm, so towards the centre of the cavity the impeller has a low effective axial stiffness, so a 1N net force on the impeller would move the impeller a large axial distance, whereas towards the soft limits the effective axial stiffness increases so that 1N net force moves the impeller a smaller axial distance.

As previously mentioned, the ability to adjust the effective axial stiffness can be beneficial for a number of reasons. For example, while a softer bearing can benefit in scenarios where additional rotor movement is advantageous, such as enhancing hydraulic balancing with axial rotor movement, increased stiffness system can be used to reduce the movement of the impeller when it is located in juxtaposition to certain positions within the housing. This can be applied to prevent the rotor from operating close to the physical housing or to some defined point within the housing, such as within 100 μm from the physical housing limit.

Where a change, and in particular an increase in effective axial stiffness is desired, the reference power can be manipulated such that further movement towards the housing or defined point is countered with a change to $IB_{Ref}$ to reduce the resulting movement, resulting in an effectively stiffer bearing. This localised change in the reference power allows for the device to operate with a normal or simulated soft bearing stiffness in some regions, while operating with a simulated stiffer bearing in others.

This effectively stiffer bearing can be practically realised by modifying the booster current $IB_{Boost}$ such that it has an opposite gradient with respect to impeller position when compared to the simulated soft bearing example. Thus, the booster current $IB_{Boost}$ can be linear, or non-linear, so choosing an appropriate quadratic or exponential relationship would allow for the simulated stiffness of the system to increase rapidly when the rotor is located close to a defined point, as shown in FIG. 5C.

Figure 6:
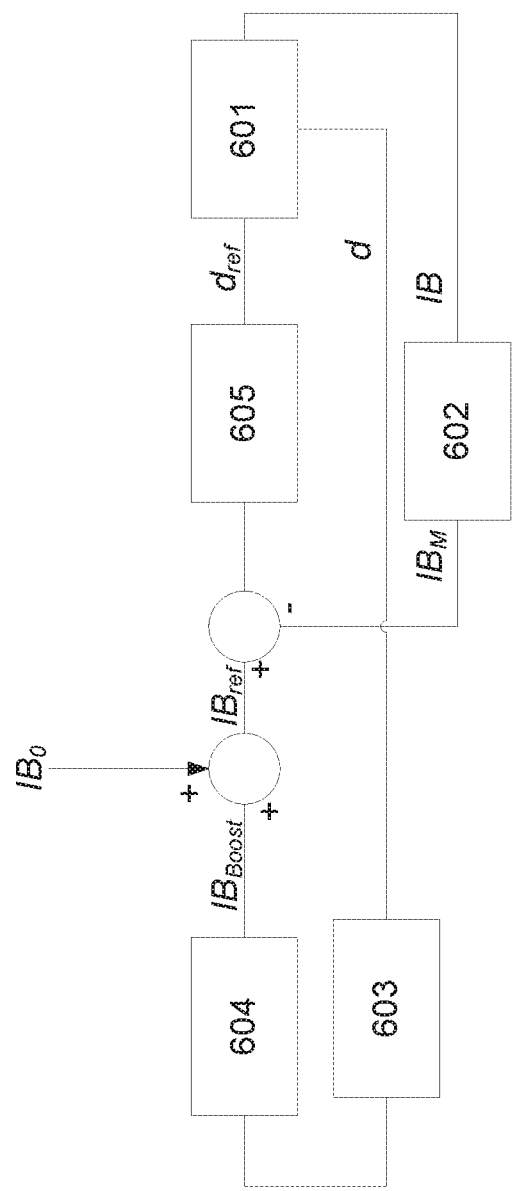
FIG. 6 is a schematic diagram illustrating a specific example of a controller architecture.

An example controller configuration is shown in FIG. 6.

In this example, the controller 150 includes a bearing controller 601 that outputs a position indication d and bearing current IB, both of which are filtered by respective low pass filters 602, 603. The filtered position is provided to a booster controller 604, which generates a booster current based on the position of the impeller 120. This is combined with a default current $IB_0$, to create a reference current $IB_{ref}$. The filtered bearing current is subtracted from the reference current $IB_{ref}$ and passed to the position controller 605, which generates a target position $d_{ref}$, which is returned to the bearing controller 601, allowing the bearing controller to control the bearing based on the current position of the impeller 120.

The movement "overreaction" was achieved by selecting a function, which increases bearing current IB with decreasing d, as shown by $IB_{Boost}$ in FIG. 5B. In a case, where the zero-power controller moves the impeller towards the left cavity, the booster adds the current $IB_{Ref}$, which moves the rotor even further to the left. A positive feedback loop is created. Stability is maintained as long as at the same distance d the gradient of $IB_{Boost}$ ($G_B$) is bigger than the gradient of the native current-displacement function $IB_{FB}$ ($G_N$). As long as this stability criteria is maintained, the booster function can have an arbitrary shape. In the current implementation it is linear to either side of P1, however different gradients, including linear and non-linear can be selected.

To limit the power consumption, the amount of the booster current was limited to ±0.5A. A manual adjustment of the rotor position is still possible by altering $IB_0$ or by modifying the attractive force of the motor through changes to the electromagnetic field.

By knowing the gradient of the native current-displacement function $G_N$, the amount of gained movement can be approximated. Without loss of generality it can be assumed that P1 is located in the origin. Consequently, for P2 (zero-power) and P3 (zero-power & Booster) the following equations can be formed:

$$G_N = \frac{IB_{Ref}}{\Delta d_3 - \Delta d_2} \quad (1)$$

$$G_B = \frac{IB_{Ref}}{\Delta d_3} \quad (2)$$

By transforming equation (2) to $IB_{Ref}$ and substituting into equation (1), the booster factor can be given with:

$$\frac{\Delta d3}{\Delta d2} = \frac{G_N}{G_N - G_B} \mid G_B > G_N \quad (3)$$

Figure 7A:
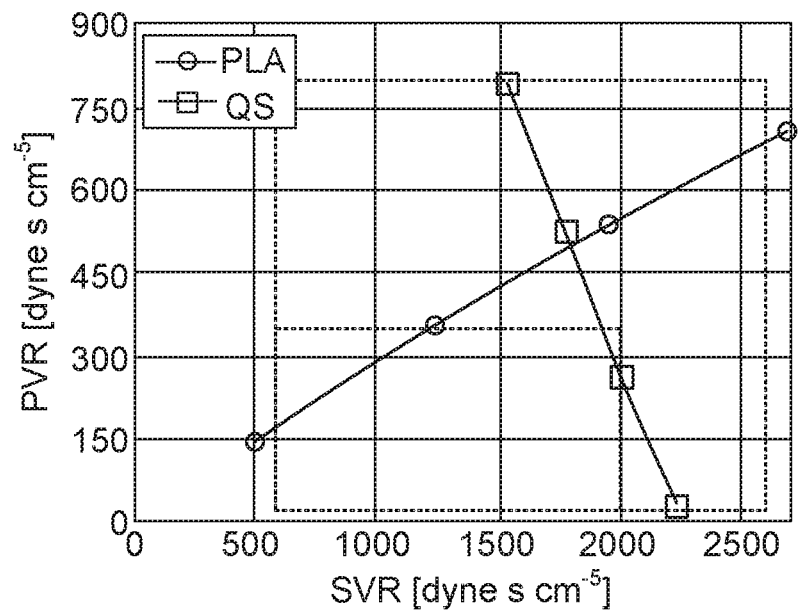
FIGS. 7A and 7B are graphs illustrating pulmonary vascular resistance and systemic vascular resistance for different axial position control algorithms.
Figure 7B:
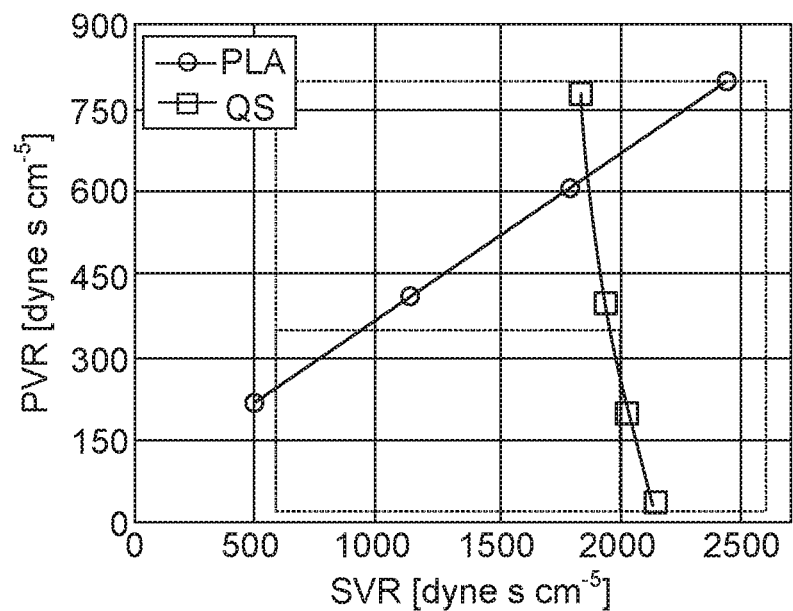

The performance of the above described approach was evaluated in-vitro by assessing the balancing ability by means of resistance boxes, shown in FIGS. 7A and 7B for standard zero-power control and the modified zero-power control (zero-power booster) described herein. Based on preliminary results the booster gains of $G_B=-2$ and −0.8 A/mm, for a movement towards left and right respectively, were selected. These values allowed to utilize the maximal movement range, while system stability is ensured. Results are shown in table 1 below:

TABLE 1

| Configuration | $A_{Mod}$ [%] | $A_{Ext}$ [%] | d [μm] |
|---|---|---|---|
| zero-power | 87.0 | 30.9 | −58 to 200 (Δd = 258) |
| zero-power Booster | 95.6 | 38.0 | −186 to 230 (Δd = 416) |

Additionally, a feasibility study was conducted in-vivo using a heart pump implanted in a calf. Pressures were measured with pressure catheters, with flows being measured using perivascular transonic flow probes.

Figure 8:
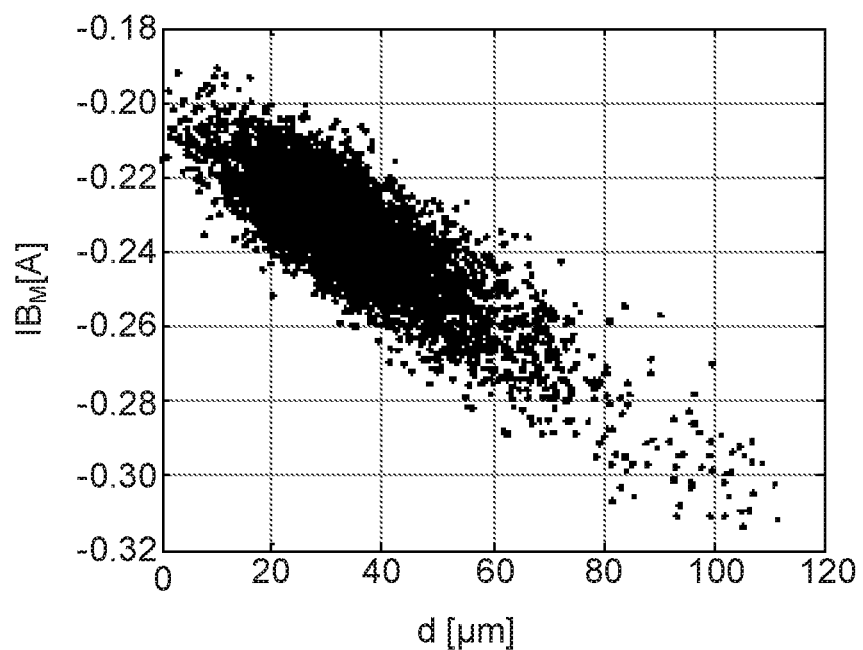
FIG. 8 is a graph illustrating measurements of a mean magnetic bearing current versus axial impeller position.

The in-vivo data were extracted from the post-operative days (POD) 1 and 2, in these two days the zero-power booster was active for 14.75 hours. In FIG. 8 the mean magnetic bearing current is plotted against the axial motor position from a 45 min phase, when the gain was −1 A/mm and speed and bias current $IB_0$ were maintained constant. By varying the bias current $IB_0$, $G_N$ was measured with −2 A/mm for this displacement range.

The additional mean power consumption of all three bearing coils, caused by the zero-power Booster, was calculated with equation 4. With $Ib_x$ as the instantaneous current in bearing X; $Ib_0$ the manual bias current; and $R_B$ the bearing resistance including drive line with a value of 2.5Ω. The bearing power consumption, averaged over the whole in-vivo time with activated zero-power Booster, was 0.13 W, with peaks up to 2 W in phases of high PVR.

$$\overline{P_B} = R_B \sum_{x=1}^{3} (Ib_x - Ib_0)^2 \quad (4)$$

Figure 9A:
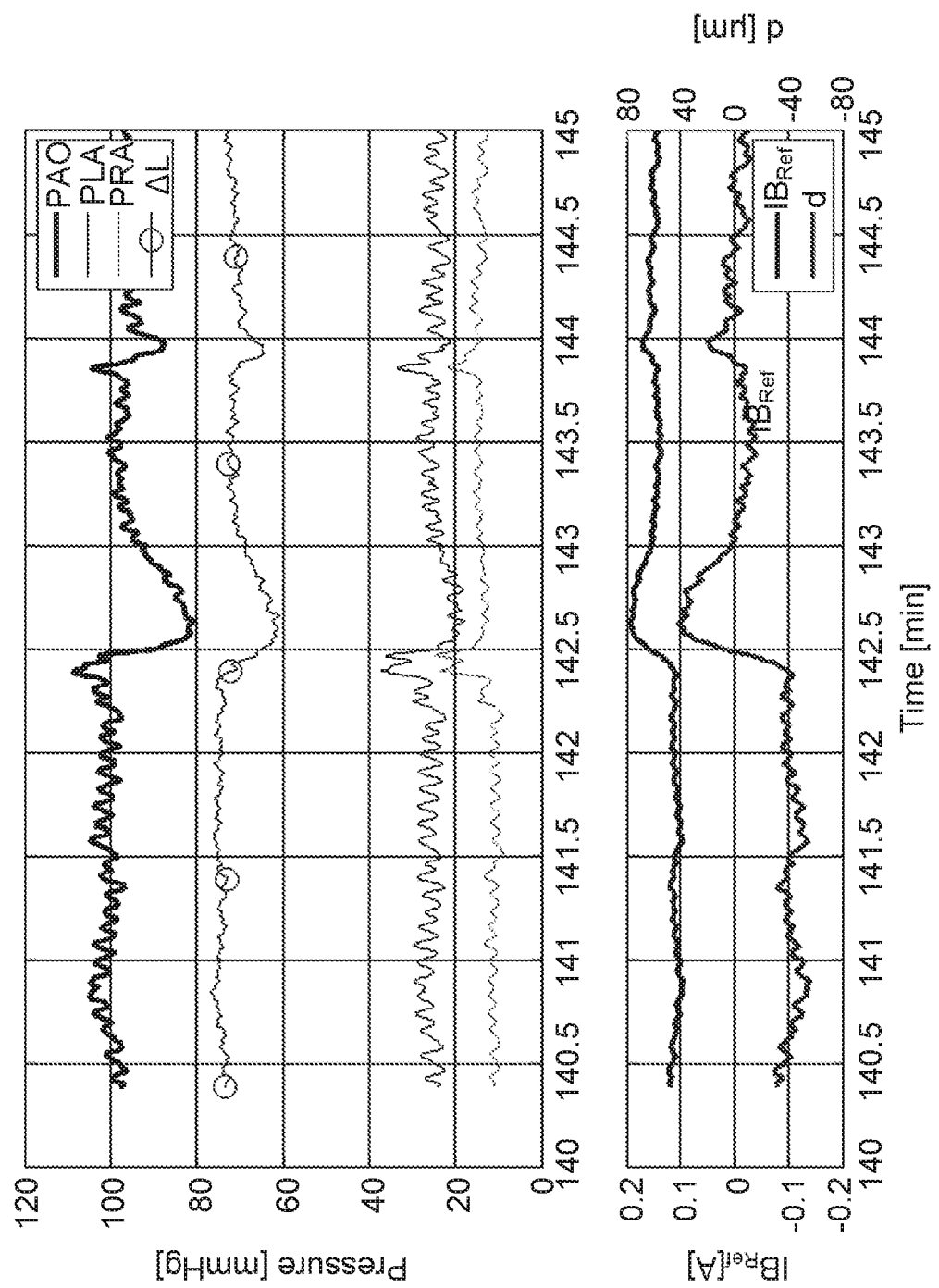
FIG. 9A is a graph illustrating the impact of a "stand-up" event on various pump parameters.

The haemodynamics, the reference current $IB_{Ref}$ and the axial rotor position (d) during a stand up event with active zero-power Booster is shown in FIG. 9A. Shortly after the stand-up event, both PAO (aortic pressure) and PLA (left atrial pressure) are decreased, while PRA (right atrial pressure) is increased. In order to redistribute the pooled right atrial blood volume, the impeller moves towards the right side. Within less than one minute the aortic pressure recovers. In this case the rotor translated by ~80 μm towards the right side. Based on equation 3, with $G_B=-1$ A/mm and an approximated $G_N=-2$A/mm, this was a 100% improvement.

Figure 9B:
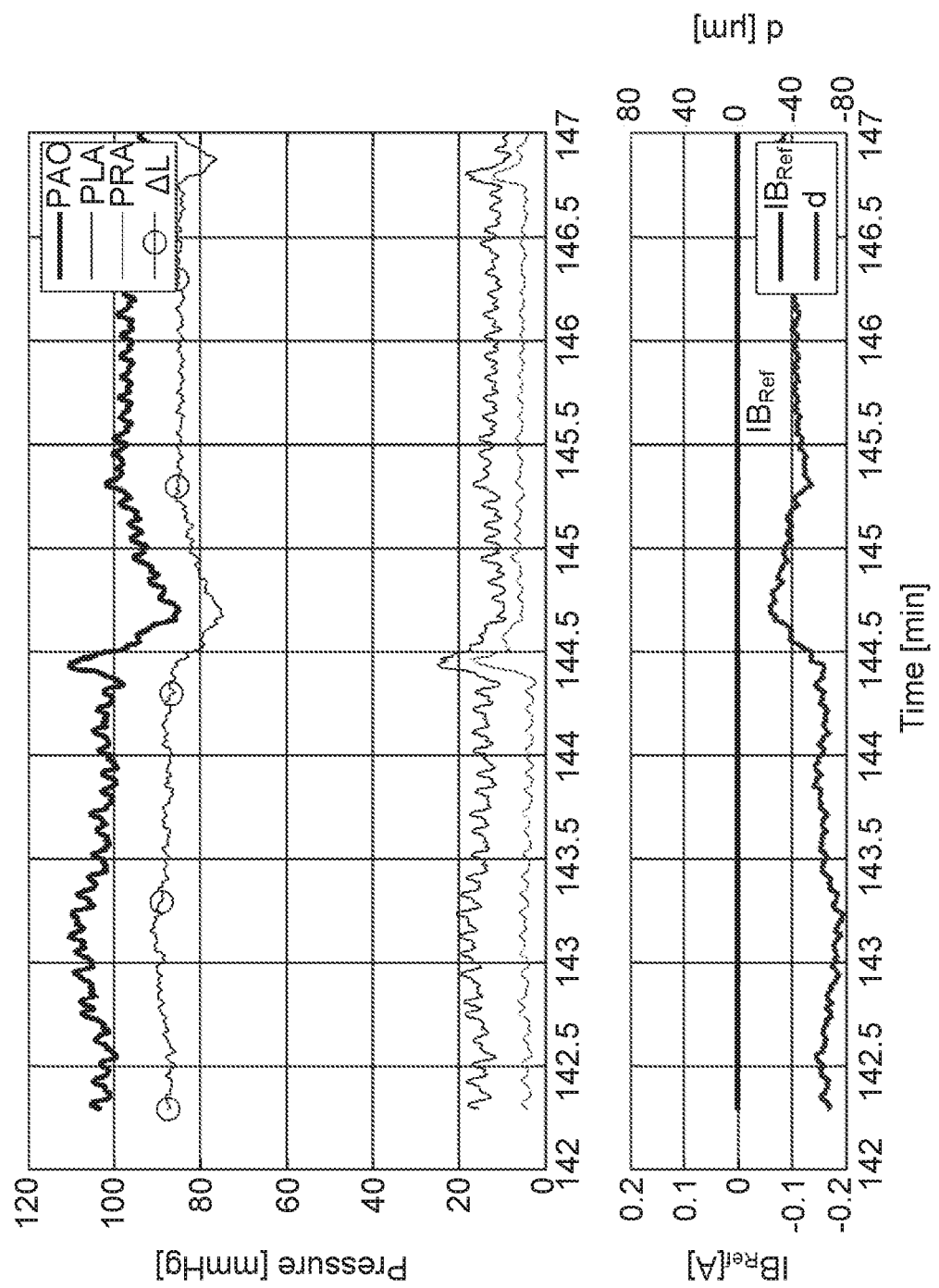
FIG. 9B is a graph illustrating the impact of a "stand-up" event on various pump parameters for a traditional zero power controller.

In FIG. 9B a stand up event without booster algorithm is plotted. Since only the VZP controller was active, the reference current IBRef was maintained constant at 0 A. Consequently, when the results from FIGS. 9A and 9B are compared, then the rotor's travelled distance increased from 40 μm to 80 μm and the achieved drop in the left pump pressure difference (deltaL) increased from 12 mmHg to 14 mmHg, for without and with the booster algorithm respectively. The larger drop in deltaL aims to reduce the drop in PLA, which can ultimately reduce the risk for left atrial suction.

Accordingly, the above described control approach allows a stiff and robust magnetic bearing system to be implemented, while allowing the impeller axial positional response to changes in hydraulic forces to be controlled independently. Consequently, an amplified or dampened response, can be realized. In contrast to the zero-power controller response this behaviour can be reprogrammed after the device design and during device operation and can be varied based on rotor position within the casing. The results demonstrated that the rotor's axial movement range improved and thereby the physiological response. The required additional energy was marginal and yet can result in significant patient benefit, in particular allowing the impeller position to be adjusted rapidly to the physiological requirements of the patient.

Whilst the above have focused in simulating a softer bearing, with enhanced axial movement for a change in force, it will be appreciated that this is not essential, and any form of control strategy can be used by changing the function used to determine the modified reference power, and hence the ultimate position to which the impeller moves.

In the above described arrangement, the controller 150 implements a bearing control strategy that controls a position of the impeller 120 in accordance with a reference power, with the reference power being set in accordance with an axial position of the impeller within a cavity. However, this is not essential, and the reference power could alternatively or additionally be set based on other operating characteristics of the heart pump.

In this regard, the bearing control approach typically takes a finite amount of time to respond to changes in the hydraulic forces/motor attractive forces acting on the impeller. In the event that it is known that the hydraulic forces are to change, this can be accommodated by adjusting the reference power, so that the bearing axial position is adjusted in advance of, or during, the change. Whilst such changes in hydraulic force can arise for any one of a number of reasons, such as changes in a physiological state of the subject, these are typically difficult to anticipate, so more typically this is as a result of changes in pump operating parameters that can be anticipated in advance of these occurring, for example by virtue of these being controlled by the controller.

In one particular example, the changes in parameters include a change in the rotational speed of the impeller. In this regard, a change in rotational speed of the impeller results in changes in flow and hence pressure within the left and right pumps, which in turn changes a pressure differential across the impeller, in turn resulting in a net hydraulic force. It will also be appreciated that speed changes will also result in a change in the hydraulic forces on a single sided impeller used in a VAD application, and accordingly, this is not intended to be limited to Biventricular (BiVAD/TAH) configurations. Additionally, changes in rotational speed necessitate changes in the magnetic field generated by the drive, which in turn result in a change in attractive forces between the drive 130 and impeller 120. It will be appreciated that such changes arise for general changes in rotational speed, as well as pulsing in rotational speed, as may be required for example to mimic a human pulse.

In one particular example, the changes in parameters include a change in the rotational speed of the impeller. In this regard, due to the increased strength of the magnetic field required to increase the motor speed or maintain a higher load the axial attractive force between the motor and the rotor would increase. The magnitude of this increase a function of the motor design, the motor control algorithm and the rate of speed change.

In any event, in one example, the controller determines pump operating parameter changes that will cause a change in hydraulic forces on the impeller, determines a reference power in accordance with the pump operating parameter changes and controls the magnetic bearing to cause the impeller to move until a bearing power indicator indicative of the power used by the magnetic bearing reaches the reference power.

In one particular example, the controller determines a change in rotational speed of the impeller and determines the reference power (current or voltage) and/or position in accordance with the change in rotational speed of the impeller, with the controller controlling the magnetic bearing in accordance with the reference power either prior to or during the change in rotational speed of the impeller. This allows the changes to hydraulic forces/motor attractive forces arising due to the change in rotational speed of the impeller to be accommodated by the magnetic bearing more rapidly than would otherwise be the case.

Figure 10A:
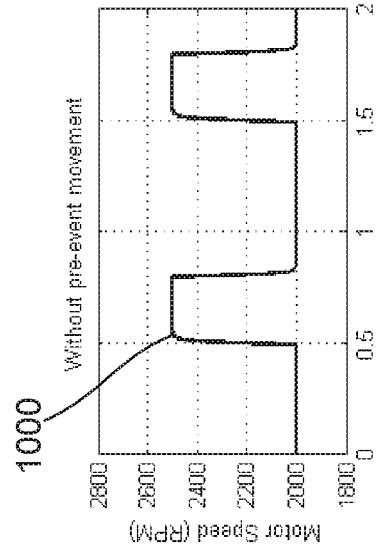
FIGS. 10A to 10C are graphs illustrating an example of rotational speed, bearing reference current and actual bearing current when reference power is not dependent on anticipated changes impeller speed.
Figure 10B:
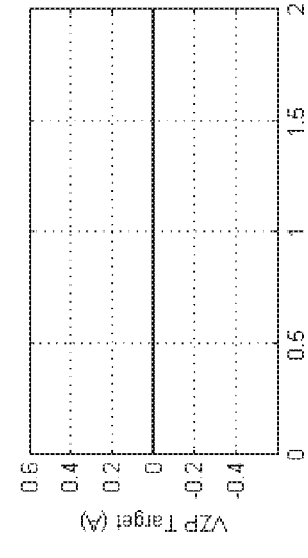
Figure 10C:
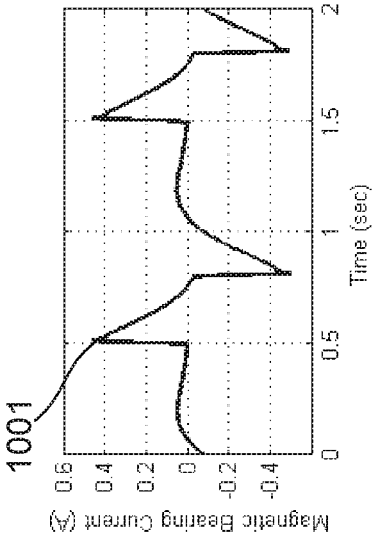
Figure 10D:
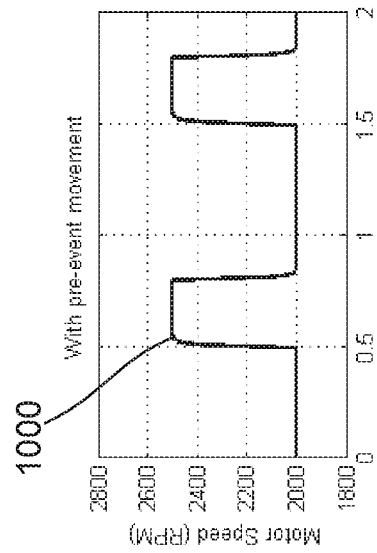
FIGS. 10D to 10F are graphs illustrating an example of rotational speed, bearing reference current and actual bearing current when reference power is set based on anticipated changes in impeller speed; and,
FIGS. 11A to 11C are graphs illustrating examples of rotational speed, bearing reference current and actual bearing current measured during in-vitro experiments.
Figure 10E:
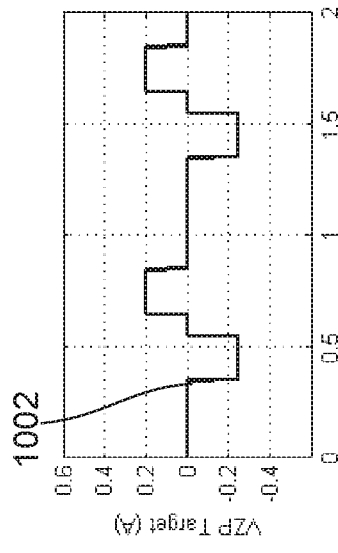
Figure 10F:
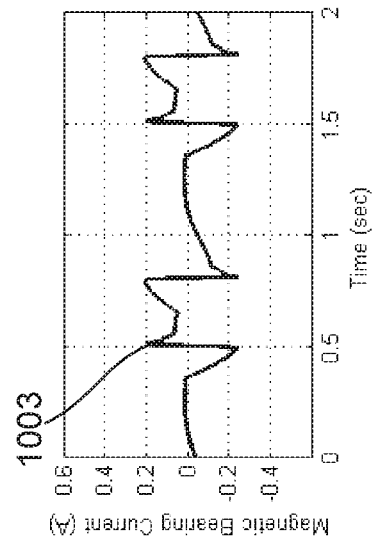

FIGS. 10A to 10C and 10D to 10F illustrate an example of the effect of changes in rotational speed of an impeller on the resulting magnetic bearing current used for a situation in which a target reference current remains unchanged (FIGS. 10A to 10C) and in which the target reference current is varied pre-emptively in anticipation of a periodic rotational speed change (FIGS. 10D to 10F). In this regard, a periodic variation of impeller rotational speed shown generally at 1000, causes a change of both hydraulic forces and motor attractive forces. When the reference current is not varied in conjunction with the motor speed change, as shown in FIG. 10B, the peak current required by the magnetic bearing to stabilise the impeller position is 0.4 A, as shown at 1001. In contrast if the reference current is varied in a compliant manner, in advance of the speed change, as shown at 1002 in FIG. 10E, then the maximum current required by the bearing is reduced to 0.2 A, as shown at 1003 in FIG. 10F.

Figure 11D:
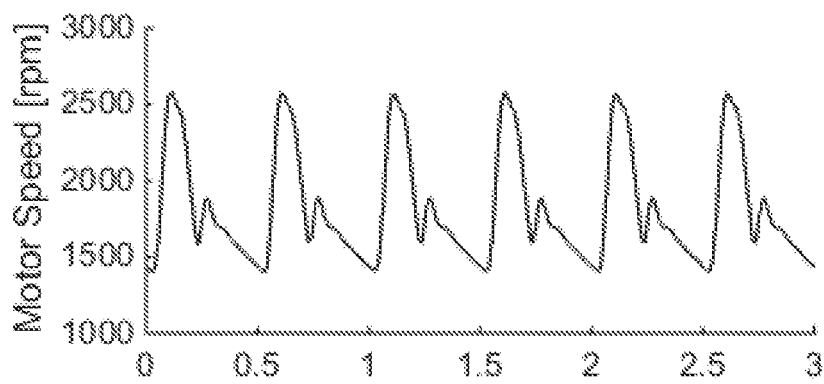
FIGS. 11D to 11G are graphs illustrating examples of rotational speed, bearing reference current, impeller position and actual bearing current measured during in-vitro experiments.
Figure 11E:
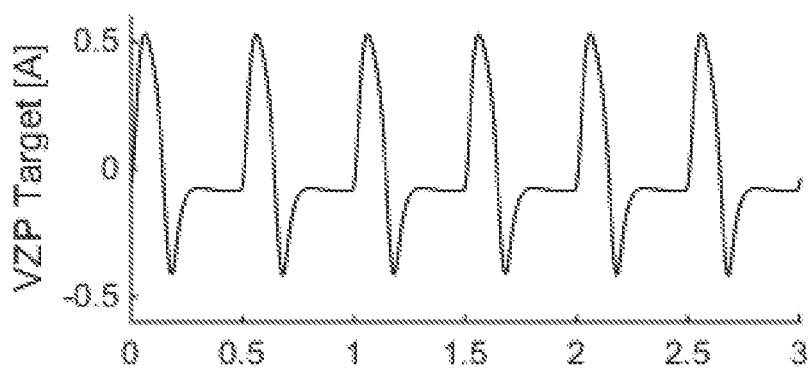
Figure 11F:
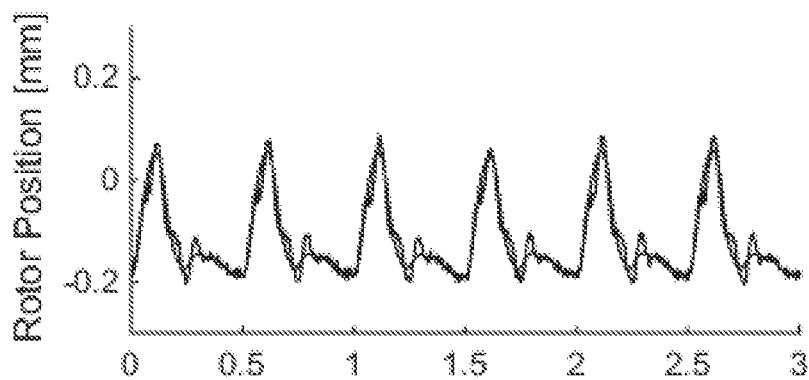
Figure 11G:
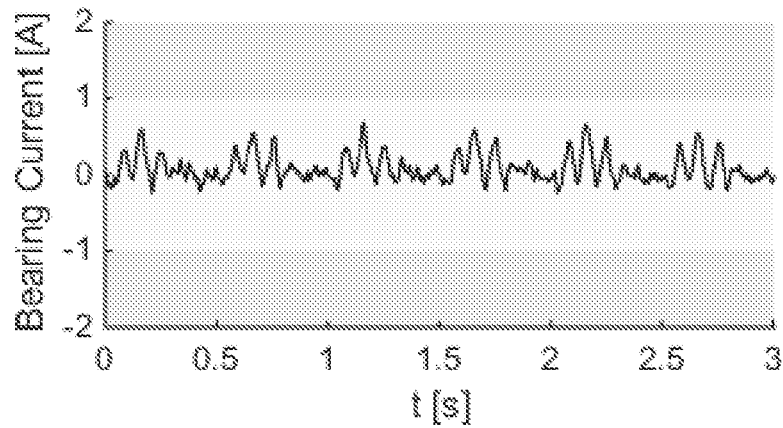

Similar effects are shown in FIGS. 11A to 11C, which illustrate the effect of changes in rotational speed of an impeller on the resulting magnetic bearing current used for a situation in which a target reference current is not adjusted based on the rotational speed (dotted lines) and a situation in which the reference current is varied in anticipation of changes in impeller rotational speed (solid line). FIGS. 11D to 11G show similar examples of the reference power being controlled based on the impeller rotational speed. This can be used to counteract movement of the impeller resulting from changes in magnetic forces associated with the magnetic drive as the rotational speed of the impeller is adjusted.

It will be appreciated that this approach can be implemented in parallel with the above described control technique, in which case the reference power is also determined in accordance with an axial position of the impeller within the cavity. However, this is not essential, and alternatively the reference power can be controlled solely based on other operating parameters of the pump.

In another example, one aspect of the invention can provide a heart pump substantially as defined above, without necessarily requiring a sensor to sense an impeller position. In this example, the controller can determine an impeller indicator indicative of operation of the impeller within the cavity, determine a reference power in accordance with the determined impeller indicator and control the magnetic bearing to cause the impeller to move until a bearing power indicator indicative of the power used by the magnetic bearing reaches the reference power.

The impeller indicator could include an impeller position, but may additionally and/or alternatively include an impeller rotational speed.

In the above examples, the bearing power indicator is based on a filtered version of the raw bearing current, which in particular is filtered, for example by a low pass filter, notch filter, band stop or a combination. The filter can be designed to prevent high or unwanted frequency current/power changes from moving the impeller. For example, due to the unbalanced nature of the impeller there may be some axial vibration and oscillation at the particular rotational frequencies. The magnetic bearing current changes in response to this vibration, so without an appropriate filter, this harmonic oscillation in the current signal could then cause the impeller position target to be moved in response, which in turn could add to the vibration amplitude at that frequency. The same issue could occur for higher frequency current changes such as noise. However, use of a low pass or other appropriately designed filter ensures that only changes in the bearing current within the relevant range would cause the impeller to move via control of the bearing power indicator to the reference power, whilst changes in the bearing current with a higher frequency would not alter the position.

In one example, the cut-off frequency of the low pass filter can be set low so the impeller position only changes due to slow changes in the pressure, as would be expected from hemodynamic changes, such as changes in systemic and pulmonary vascular resistances. In this control strategy higher frequency changes (such as suction and pulsing) would not change the impeller position because of their relatively high frequency, instead the bearing current would change significantly as the system tried to maintain the impeller position. An example of this is shown in FIG. 12A, in which relatively high changes in bearing current are observed for given changes in impeller position.

In another example, by increasing the cut-off frequency the impeller can move the reference power target in response to higher frequency disturbances such as suction and pulsing. This can provide significant benefits, for example when pulsing, as shown in FIG. 12D, because changes in the bearing current are reduced and the system can stabilize high pulse magnitudes. This can reduce the effectiveness of using changes in bearing current to detect suction events, as described in application U.S. Ser. No. 62/275,723, meaning suction events might instead need to be detected based on the impeller axial movement.

Figures 12A, 12B:
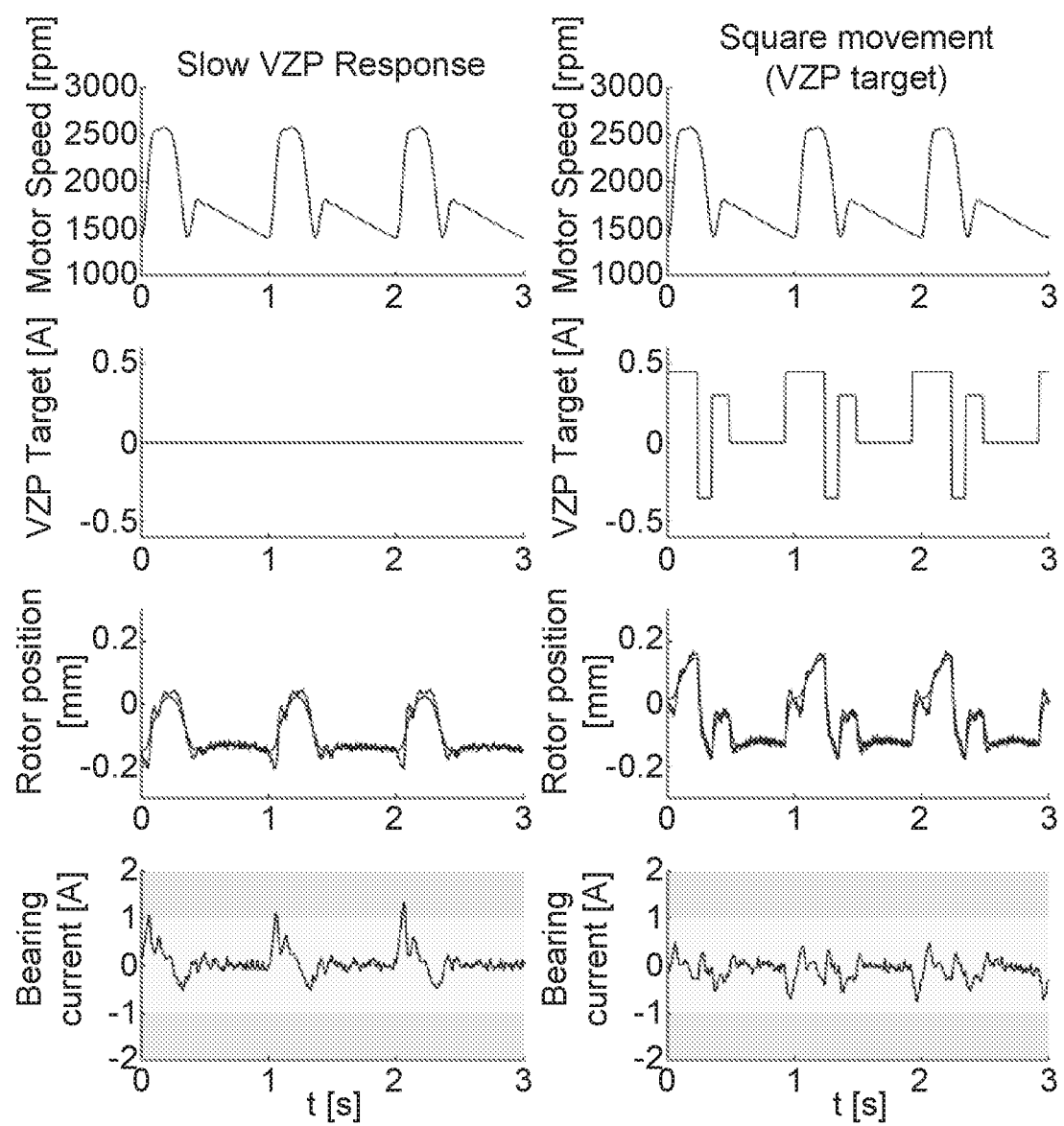
FIGS. 12A to 12D are graphs illustrating examples of the responsiveness of different impeller positional control strategies.
Figure 12C:
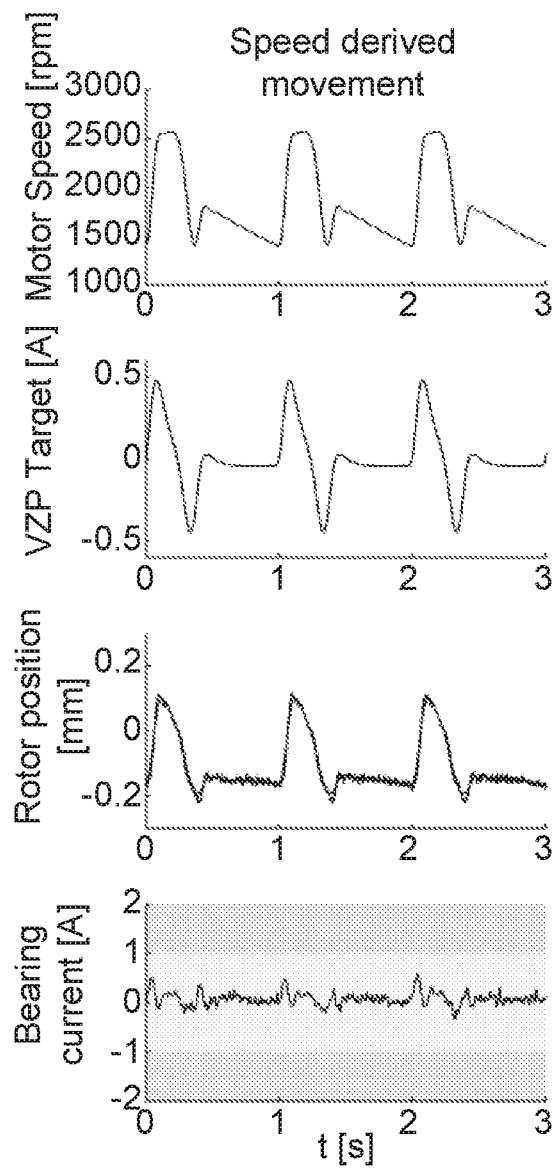
Figure 12D:
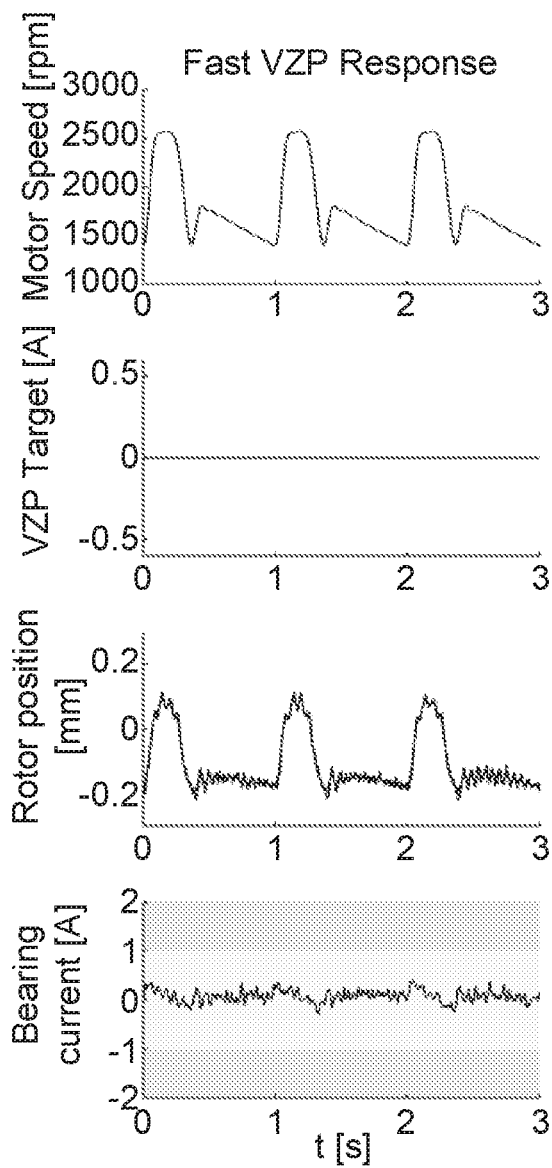

In contrast, if the reference power is adjusted as described above, based on either the impeller position or speed, as shown in FIGS. 12B and 12C, this provides a compromise in that the bearing stiffness can be controlled so that less current is used by the bearing, and high pulse amplitudes can be stabilised. Despite this, suction events are still detectable from changes in bearing current and its deviation from the reference value, allowing this to be used when controlling impeller rotational speed. So, changing the reference power can result in advantages of the higher cut-off frequency whilst allowing suction events to be detected.

It should be noted that whilst the filter is the most important parameter in the above described arrangement, operation of the position controller 605 can also have an impact.

The above described arrangement can be employed in wide range of circumstances and in different pump configurations. For example, this can be used when one or two pumps are used to provide assistance or replacement of the left or right ventricles, including in a TAH, when two rotary pumps to provide complete replacement of the native heart, in an LVAD/RVAD, when a single rotary pump is used to provide assistance to either the left or right ventricles, or in a BiVAD, when two rotary pumps to provide assistance to either the left or right ventricles.

An example of a single VAD heart pump will now be described with reference to FIGS. 13A to 13F.

In this example, the heart pump 1300 includes a housing 1310 defining a cavity 1315. The housing can be of any suitable form but typically includes a main body, and left and right end caps which connect to the main body. The housing can be made of any suitable biocompatible material, and can be made of titanium, a polymer or the like.

The housing 1310 includes an inlet 1311, for connection to the left atrium/pulmonary vein or right atrium/vena cava, or left or right ventricle, and an outlet 1313 for connection to the aorta or pulmonary artery, respectively.

The heart pump 1300 includes an impeller 1320 provided within the cavity 1315. The impeller 1320 includes a rotor 1321 having vanes mounted thereon for urging fluid from the inlet 1311 to the outlet 1312 upon rotation of the impeller 1320. In this example, as the heart pump 1300 is a single ventricular assist device, the impeller includes a single set of vanes 1322 for urging fluid from the inlet 1311 to the outlet 1312. In this example, the vanes 1322 have a configuration similar to that described above with respect to FIGS. 11I and 11J, and these will not therefore be described in further detail, although it will be appreciated that other suitable vane configurations can be used. The impeller can also include an aperture 1324 extending therethrough to allow blood to flow around the rear surface of the impeller and thereby prevent stagnation and clotting of blood within the heart pump. Furthermore, the use of a magnetic bearing in this region allows for blood gaps in excess of 200-300 μm, which can both reduces shear stress and thus red cell lysis, as well as promote greater rates of washout flow than otherwise anticipated in gaps created by hydrodynamic bearings.

The heart pump 1300 further includes a drive 1330 that rotates the impeller 1320 within the cavity 1315. The drive 1330 can be of any appropriate form but typically includes a number of coils 1331, each wound on a respective stator 1332, supported by a mounting 1333, allowing the drive 1330 to be coupled to the housing 1310. The drive cooperates with magnetic material 1334 mounted in the rotor 1321, with the magnetic material being in the form of a number of circumferentially spaced permanent drive magnets arranged proximate an outer circumferential edge of the rotor 1321. In one example, the coils 1331 and stators 1332 are wedge shaped and circumferentially spaced around the mounting 1333, so as to provide twelve electromagnets radially aligned with the drive magnets 1334 in the rotor 1321, to thereby maximise a degree of magnetic coupling between the magnets in the rotor 1321 and the drive 1330.

The heart pump 1300 can further include a magnetic bearing 1340 including at least one bearing coil 141 that controls an axial position of the impeller within the cavity 1315. In one particular example, shown in more detail in FIG. 13E, the magnetic bearing includes three bearing coils 1341, each of which is mounted on a first leg 1342.1 of respective U-shaped stators 1342, with a second leg 1342.2 being positioned radially inwardly of the first leg 1342.1. The stators 1342 are mounted to or integrally formed with a support 1343 and circumferentially spaced 120° apart around the housing so that the first and second legs 1342.1 1342.2 align with respective magnetic material, such as bearing magnets 1344, 1345 within the impeller 1320, allowing an axial position of the impeller 1320 to be controlled.

In one particular example, the bearing rotor assembly includes ferromagnetic core target 1344 mounted in the rotor, proximate an outer circumferential edge of the rotor 1321, and a permanent bearing magnet or ferromagnetic material 1345 mounted radially inwardly of the first ferromagnetic core target 1344, so that the ferromagnetic core target and bearing magnets 1344, 1345 align with respective legs 1342.1, 1342.2 of the stators 1342. The ferromagnetic core target can be replaced with a second permanent magnet. However, the use of a magnetic bearing may not be required and can be replaced by a static physical bearing or hydrodynamic bearing, or the like.

Figure 13A:
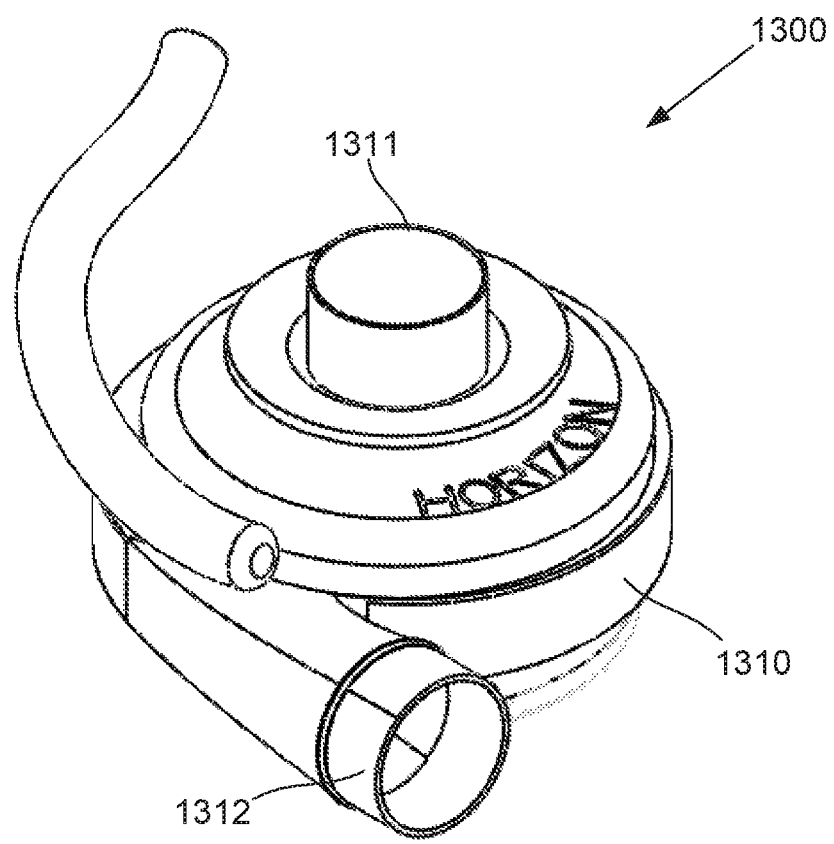
FIG. 13A is a schematic perspective view of an example of a single VAD heart pump.
Figure 13B:
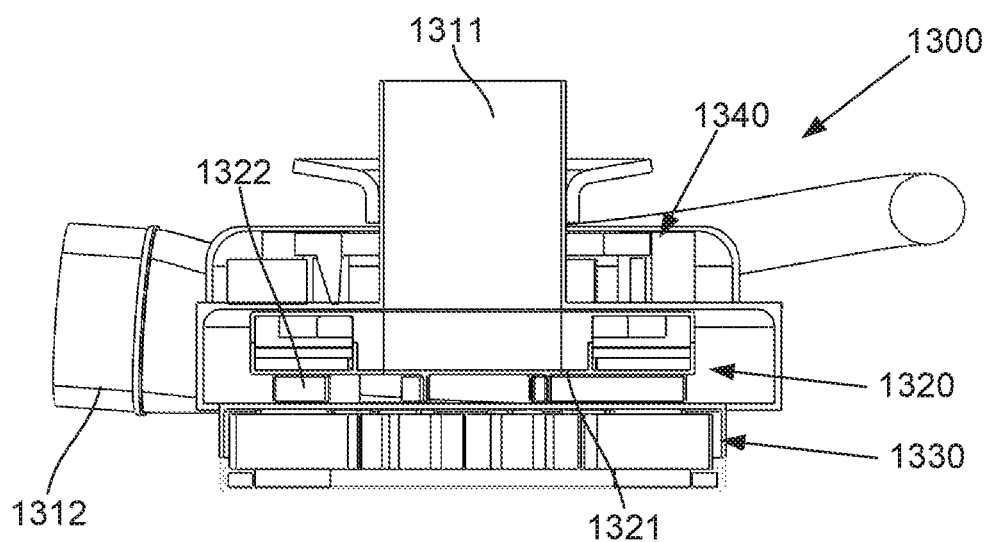
FIG. 13B is a schematic cutaway side view of the heart pump of FIG. 13A.
Figure 13C:
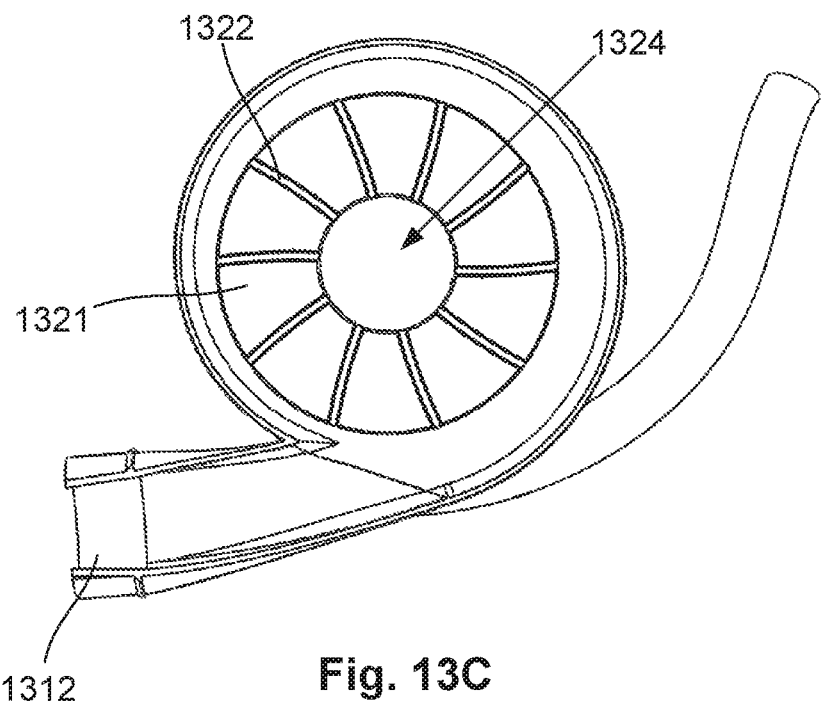
FIG. 13C is a schematic cutaway plan view of the heart pump of FIG. 13A.
Figure 13D:
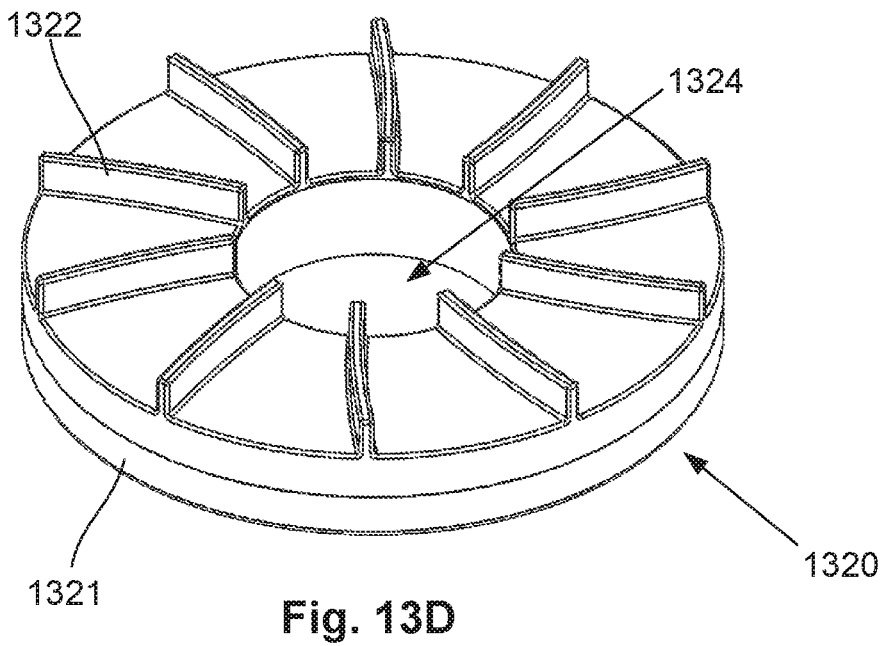
FIG. 13D is a schematic perspective view of the impeller of the heart pump of FIG. 13A.
Figure 13E:
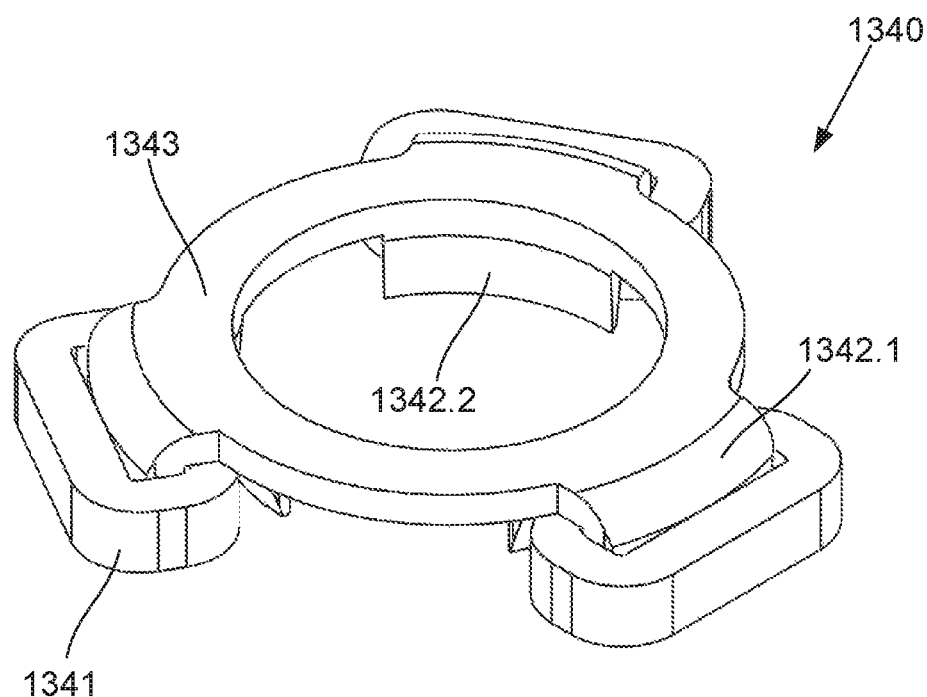
FIG. 13E is a schematic perspective view of the magnetic bearing of the heart pump of FIG. 13A; and,
FIG. 13F is a schematic cutaway perspective view of the impeller of FIG. 13A.
Figure 13F:
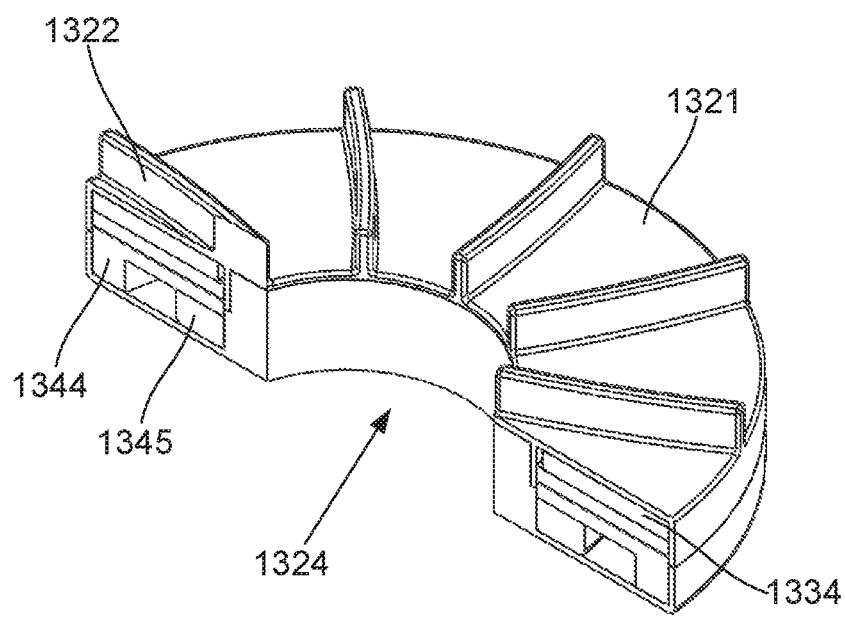

In this example, the drive 1330 and magnetic bearing 1340 are mounted at opposing ends of the housing 1310 so that the drive and bearing 1330, 1340 are provided proximate opposing surfaces of the rotor 1321 as shown for example in FIG. 13B. In the current example the drive 1330 is mounted adjacent the side of the impeller 1320 that includes vanes so as to maximise the blood gap between the rotor, vanes and the casing. That is to say, only the vane tips are in closer proximity to the casing, however this blood gap can still be in the order of 200-300 µm. Additionally, bearing and drive are configured so that the magnetic forces inherent between the drive 1330 and impeller 1320, and between the magnetic bearing 1340 and impeller 1320 and the hydraulic forces on the impeller 1320 define a balance position within the cavity under conditions of normal flow. This minimises the bearing current required to maintain the position of the impeller 1320 within the cavity under nominal flow conditions.

It will be appreciated as in the previous example, the apparatus can further include a controller, and otherwise functions largely as previously described, and hence will not be described in further detail.

The controller and control process can also be used in a device in conjunction with other control arrangements, such as those that use an active speed controller that controls the rotational speed of the impeller.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

Persons skilled in the art will appreciate that numerous variations and modifications will become apparent. All such variations and modifications which become apparent to persons skilled in the art, should be considered to fall within the spirit and scope that the invention broadly appearing before described, including equivalents.

What is claimed is:

1. A heart pump including:
   a) a housing defining a cavity including at least one inlet and at least one outlet;
   b) an impeller provided within the cavity, the impeller including vanes for urging fluid from the inlet to the outlet upon rotation of the impeller;
   c) a drive that rotates the impeller within the cavity;
   d) a magnetic bearing including at least one bearing coil that controls an axial position of the impeller within the cavity; and,
   e) a controller including an electronic processing device that:
      i) determines an impeller indicator indicative of operation of the impeller within the cavity;
      ii) determines a reference power in accordance with the determined impeller indicator; and,
      iii) controls the magnetic bearing by energizing the at least one bearing coil with a bias current to cause the impeller to move to a new target axial position with the target position being iteratively adjusted until a bearing power indicator indicative of the power used by the magnetic bearing reaches the reference power.

2. A heart pump according to claim 1, wherein the impeller indicator is indicative of at least one of:
   a) an axial position of the impeller within the cavity; or
   b) a rotational speed of the impeller within the cavity.

3. A heart pump according to claim 1, wherein the heart pump includes a sensor that senses an axial position of the impeller within the cavity and wherein, in response to a change in axial hydraulic forces on the impeller, the controller:
   a) determines an axial position of the impeller within the cavity;
   b) determines a reference power in accordance with the determined axial position; and,
   c) controls the magnetic bearing to cause the impeller to move until a bearing power indicator indicative of the power used by the magnetic bearing reaches the reference power.

4. A heart pump according to claim 1, wherein a change in hydraulic forces generates a resulting force acting on the impeller in a first axial direction and wherein the controller controls the magnetic bearing to move the impeller in a second axial direction opposite to the first axial direction.

5. A heart pump according to claim 1, wherein the controller determines changes in axial hydraulic forces within the cavity by at least one of:
   a) detecting axial movement of the impeller within the cavity; or
   b) detecting changes in the bearing power indicator required to maintain the impeller at a constant axial position within the cavity.

6. A heart pump according to claim 5, wherein the controller determines the changes in axial hydraulic forces by filtering a bearing current signal using at least one of:
   a) a low pass filter;
   b) a notch filter; or
   c) a band stop filter.

7. A heart pump according to claim 6, wherein the low pass filter has a cut-off of at least one of:
   a) between 0.1-10 Hz;
   b) between 1-15 Hz;
   c) between 15-30 Hz;
   d) approximately 15 Hz;
   e) approximately 30 Hz;
   f) approximately 1 Hz; or
   g) between 30-100 Hz.

8. A heart pump according to claim 1, wherein the controller iteratively moves the impeller by repeatedly:
   a) controlling the magnetic bearing to move the impeller to a new axial position in accordance with the reference power; and,
   b) modifying the reference power in accordance with the new axial position of the impeller.

9. A heart pump according to claim 8, wherein the controller iteratively moves the impeller until at least one of:
   a) the reference power reaches a defined threshold;
   b) the axial position of the impeller reaches a defined threshold; or
   c) the hydraulic forces are at least one of:
      i) balanced; or
      ii) reversed.

10. A heart pump according to claim 8, wherein the controller modifies the reference power by progressively increasing a magnitude of the reference power by a progressively smaller amount for each iteration.

11. A heart pump according to claim 1, wherein the controller:
   a) controls the magnetic bearing to cause the impeller to move to a target axial position;
   b) determines if the bearing power indicator is at the reference power; and,
   c) if the bearing power indicator is not at the reference power;
      i) determines a new axial position of the impeller;
      ii) determines a reference power in accordance with the new axial position;
      iii) uses the reference power to determine a target axial position; and,
      iv) repeats steps a) to c) until the bearing power indicator reaches the reference power.

12. A heart pump according to claim 1, wherein the controller includes:
   a) a bearing controller that:
      i) uses signals from a position sensor to determine a current axial position of the impeller;
      ii) controls the current supplied to the magnetic bearing to thereby maintain the impeller at a target axial position; and,
      iii) outputs the bearing power indicator and current axial position; and,
   b) a position controller that:
      i) uses the bearing power indicator and current axial position of the impeller to determine the target axial position; and,
      ii) provides the target axial position to the bearing controller.

13. A heart pump according to claim 1, wherein the impeller includes first and second sets of vanes provided on a rotor body, the rotor being positioned within the cavity to define:
   a) a first cavity portion having a first inlet and a first outlet, the first set of vanes being provided within the first cavity portion so as to define a first pump that provides at least partial left ventricular function; and,
   b) a second cavity portion having a second inlet and a second outlet, the second set of vanes being provided within the second cavity portion so as to define a second pump that provides at least partial right ventricular function and wherein at least one of:
      i) the axial position of the impeller determines a separation between each set of vanes and a respective cavity surface, the separation being used to control the fluid flows from the inlets to the outlets; or
      ii) the first and second pumps have respective pump performance curve having different gradients so that a change in rotational speed of the pump causes a change in the relative flows of the first and second pumps.

14. A heart pump according to claim 1, wherein:
   a) the drive includes:
      i) a number of circumferentially spaced permanent magnets mounted in a rotor of the impeller, adjacent magnets having opposing polarities; and,
      ii) at least one drive coil that in use generates a magnetic field that cooperates with the magnetic material allowing the impeller to be rotated; and,
   b) the magnetic bearing is positioned at a second end of the cavity and includes:
      i) first and second annular magnetic bearing members mounted within and proximate a second face of the rotor, the first magnetic bearing member being provided radially outwardly of the second magnetic bearing member;
      ii) a number of circumferentially spaced substantially U-shaped bearing stators mounted in the housing proximate the second end of the cavity, each U-shaped bearing stator having first and second bearing stator legs substantially radially aligned with the first and second magnetic bearing members respectively; and,
      iii) at least one bearing coil on each bearing stator that generates a magnetic field that cooperates with the magnetic bearing members to thereby at least one of:
         (1) control an axial position of the impeller; or
         (2) at least partially restrain radial movement of the impeller.

15. A heart pump according to claim 1, wherein the heart pump is at least one of:
   a) a ventricular assist device; or
   b) a total artificial heart.

16. A heart pump according to claim 1, wherein the controller:
   a) determines pump operating parameter changes that will cause a change in at least one of hydraulic forces or motor attractive forces on the impeller;
   b) determines a reference power in accordance with the pump operating parameter changes; and,
   c) controls the magnetic bearing to cause the impeller to move until a bearing power indicator indicative of the power used by the magnetic bearing reaches the reference power.

17. A heart pump according to claim 16, wherein the controller:
   a) determines a change in rotational speed of the impeller;
   b) determines the reference power in accordance with the change in rotational speed of the impeller; and
   c) controls the magnetic bearing in accordance with the reference power, at least one of:
      i) prior to the change in rotational speed of the impeller; or
      ii) during the change in rotational speed of the impeller.

18. A heart pump according to claim 16, wherein the controller:
   a) determines an axial position of the impeller within the cavity; and, b) determines the reference power in accordance with the determined axial position and the pump operating parameter changes.

19. A controller for a heart pump, the controller including an electronic processing device that:
 a) determines an impeller indicator indicative of operation of an impeller within a cavity;
 b) determines a reference power in accordance with the determined impeller indicator; and,
 c) controls a magnetic bearing by energizing at least one bearing coil with a bias current to cause the impeller to move to a new target axial position with the target position being iteratively adjusted until a bearing power indicator indicative of the power used by the magnetic bearing reaches the reference power.

20. A method for controlling a heart pump, the method including, in an electronic processing device:
 a) determining an impeller indicator indicative of operation of an impeller within a cavity;
 b) determining a reference power in accordance with the determined impeller indicator; and,
 c) controlling a magnetic bearing by energizing at least one bearing coil with a bias current to cause the impeller to move to a new target axial position with the target position being iteratively adjusted until a bearing power indicator indicative of the power used by the magnetic bearing reaches the reference power.

* * * * *